（12) United States Patent
Soni et al.

(10) Patent No.: US 11,507,822 B2
(45) Date of Patent: Nov. 22, 2022

(54) SCALABLE ARTIFICIAL INTELLIGENCE MODEL GENERATION SYSTEMS AND METHODS FOR HEALTHCARE

(71) Applicant: General Electric Company, Schenectady, NY (US)

(72) Inventors: Ravi Soni, San Ramon, CA (US); Min Zhang, San Ramon, CA (US); Gopal Avinash, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 1058 days.

(21) Appl. No.: 16/176,980

(22) Filed: Oct. 31, 2018

(65) Prior Publication Data

US 2020/0134446 A1    Apr. 30, 2020

(51) Int. Cl.
*G06G 7/00* (2006.01)
*G06N 3/08* (2006.01)
(Continued)

(52) U.S. Cl.
CPC ........... *G06N 3/08* (2013.01); *G06F 11/3447* (2013.01); *G06K 9/6256* (2013.01); *G16H 30/20* (2018.01); *G16H 50/20* (2018.01)

(58) Field of Classification Search
CPC ........ G06N 3/08; G06N 3/0472; G06N 3/084; G06N 3/0454; G06F 11/3447; G06K 9/6256; G16H 30/20; G16H 50/20; G06T 7/0012; G06T 7/0002; G06T 2207/20081; G06T 2207/20084; G06T 2207/30168
See application file for complete search history.

(56) References Cited

U.S. PATENT DOCUMENTS

| | | | | |
|---|---|---|---|---|
| 2014/0372112 A1 * | 12/2014 | Xue | ...................... | G06N 3/0454 704/232 |
| 2017/0316324 A1 * | 11/2017 | Barrett | ................... | G06N 20/20 |
| 2018/0018590 A1 | 1/2018 | Szeto | | |

FOREIGN PATENT DOCUMENTS

| | | | | |
|---|---|---|---|---|
| CA | 3035298 A1 * | 3/2018 | ............. | G06F 17/16 |
| CN | 104866727 A * | 8/2015 | ............... | G06N 3/04 |
| JP | 2017537370 A * | 12/2017 | | |

OTHER PUBLICATIONS

Karras et al., "Progressive Growing of Gans For Improved Quality, Stability, and Variation," Published as a conference paper at ICLR 2018, Feb. 26, 2018, 26 pages.

(Continued)

*Primary Examiner* — Xin Jia

(57) ABSTRACT

Systems and methods to generate artificial intelligence models with synthetic data are disclosed. An example system includes a deep neural network (DNN) generator to generate a first DNN model using first real data. The example system includes a synthetic data generator to generate first synthetic data from the first real data, the first synthetic data to be used by the DNN generator to generate a second DNN model. The example system includes an evaluator to evaluate performance of the first and second DNN models to determine whether to generate second synthetic data. The example system includes a synthetic data aggregator to aggregate third synthetic data and fourth synthetic data from a plurality of sites to form a synthetic data set. The example system includes an artificial intelligence model deployment processor to deploy an artificial intelligence model trained and tested using the synthetic data set.

20 Claims, 20 Drawing Sheets

(51) Int. Cl.
*G16H 30/20* (2018.01)
*G16H 50/20* (2018.01)
*G06F 11/34* (2006.01)
*G06K 9/62* (2022.01)

(56) References Cited

OTHER PUBLICATIONS

Kirkpatrick et al., "Overcoming catastrophic forgetting in neural networks," Jan. 25, 2017, 13 pages.
European patent application 19206349.3 filed Oct. 30, 2019—Search Report dated Mar. 16, 2020, 10 pages.

\* cited by examiner

SCALABLE ARTIFICIAL INTELLIGENCE MODEL GENERATION SYSTEMS AND METHODS FOR HEALTHCARE

FIELD OF THE DISCLOSURE

This disclosure relates generally to improved medical systems and, more particularly, to improved, scalable artificial intelligence model generation systems and methods for healthcare.

BACKGROUND

A variety of economy, technological, and administrative hurdles challenge healthcare facilities, such as hospitals, clinics, doctors' offices, etc., to provide quality care to patients. Economic drivers, less skilled staff, fewer staff, complicated equipment, and emerging accreditation for controlling and standardizing radiation exposure dose usage across a healthcare enterprise create difficulties for effective management and use of imaging and information systems for examination, diagnosis, and treatment of patients.

Healthcare provider consolidations create geographically distributed hospital networks in which physical contact with systems is too costly. At the same time, referring physicians want more direct access to supporting data in reports along with better channels for collaboration. Physicians have more patients, less time, and are inundated with huge amounts of data, and they are eager for assistance. However, large datasets are necessary for computer-driven solutions, such as neural networks and other "artificial intelligence" to assist human clinicians with analysis, optimization, improvement, and/or other decision support. Such large datasets are often missing or unobtainable with current systems and restrictions.

BRIEF SUMMARY

Certain examples provide an artificial intelligence model generation system. The example system includes a deep neural network (DNN) generator to generate a first DNN model using first real data. The example system includes a synthetic data generator to generate first synthetic data from the first real data, the first synthetic data to be used by the DNN generator to generate a second DNN model. The example system includes an evaluator to evaluate performance of the first DNN model and the second DNN model based on output of the first DNN model and the second DNN model, the evaluator to determine whether to generate second synthetic data based on a comparison of a first output of the first DNN model and a second output of the second DNN model. The example synthetic data generator is to generate third synthetic data from a first site when the comparison indicates that performance of the first DNN model and performance of the second DNN model are aligned. The example system includes a synthetic data aggregator to aggregate the third synthetic data from the first site and fourth synthetic data from a second site to form a synthetic data set. The example system includes an artificial intelligence model deployment processor to deploy an artificial intelligence model trained and tested using the synthetic data set.

Certain examples provide a computer-readable storage medium including instructions which, when executed, cause at least one processor to implement at least: a deep neural network (DNN) generator to generate a first DNN model using first real data; a synthetic data generator to generate first synthetic data from the first real data, the first synthetic data to be used by the DNN generator to generate a second DNN model; an evaluator to evaluate performance of the first DNN model and the second DNN model based on output of the first DNN model and the second DNN model, the evaluator to determine whether to generate second synthetic data based on a comparison of a first output of the first DNN model and a second output of the second DNN model, the synthetic data generator to generate third synthetic data from a first site when the comparison indicates that performance of the first DNN model and performance of the second DNN model are aligned; a synthetic data aggregator to aggregate the third synthetic data from the first site and fourth synthetic data from a second site to form a synthetic data set; and an artificial intelligence model deployment processor to deploy an artificial intelligence model trained and tested using the synthetic data set.

Certain examples provide a method including generating, using at least one processor, a first DNN model using first real data. The example method includes generating, using the at least one processor, a first synthetic data from the first real data. The example method includes generating, using the at least one processor, a second DNN model using the first synthetic data. The example method includes evaluating, using the at least one processor, performance of the first DNN model and the second DNN model based on output of the first DNN model and the second DNN model, the evaluating to determine whether to generate second synthetic data based on a comparison of a first output of the first DNN model and a second output of the second DNN model. The example method includes generating, using the at least one processor when the comparison indicates that performance of the first DNN model and performance of the second DNN model align, third synthetic data from a first site. The example method includes aggregating, using the at least one processor, the third synthetic data from the first site and fourth synthetic data from a second site to form a synthetic data set. The example method includes deploying, using the at least one processor, an artificial intelligence model trained and tested using the synthetic data set.

BRIEF DESCRIPTION OF THE DRAWINGS

The figures are not scale. Wherever possible, the same reference numbers will be used throughout the drawings and accompanying written description to refer to the same or like parts.

DETAILED DESCRIPTION

Figure 1:
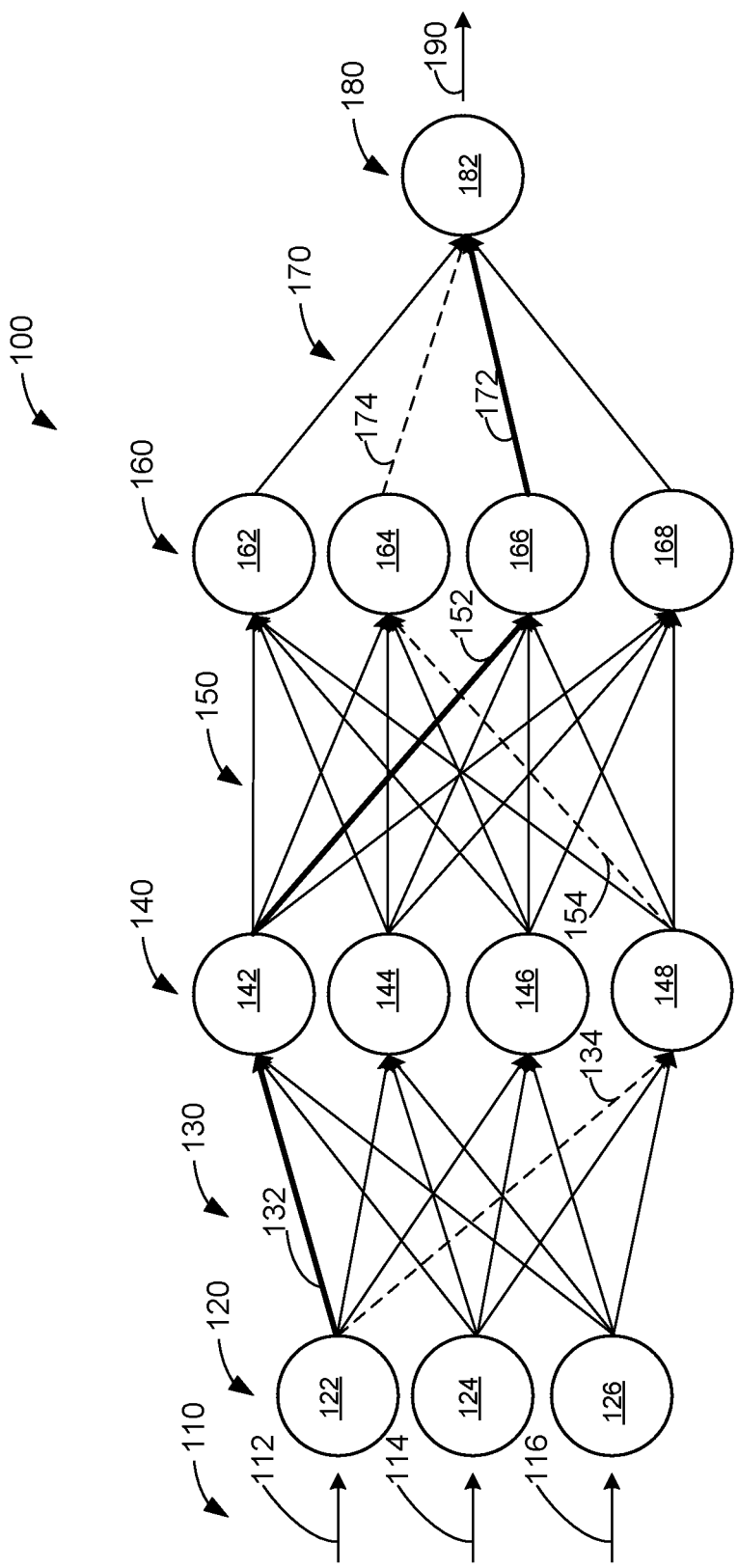
FIG. 1 is a representation of an example deep learning neural network.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment. For example, certain examples can be applied to non-medical imaging such as non-destructive testing, explosive detection, etc.

I. Overview

Medical data can be obtained from imaging devices, sensors, laboratory tests, and/or other data sources. Alone or in combination, medical data can assist in diagnosing a patient, treating a patient, forming a profile for a patient population, influencing a clinical protocol, etc. However, to be useful, medical data must be organized properly for analysis and correlation beyond a human's ability to track and reason. Computers and associated software and data constructs can be implemented to transform disparate medical data into actionable results.

For example, imaging devices (e.g., gamma camera, positron emission tomography (PET) scanner, computed tomography (CT) scanner, X-Ray machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine learning can be used to help configure, monitor, and update the medical imaging workflow and devices.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network (DLN), also referred to as a deep neural network (DNN), can be a training network (e.g., a training network model or device) that learns patterns based on a plurality of inputs and outputs. A deep learning network/deep neural network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Deep Learning

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning. However, a larger dataset results in a more accurate, more robust deployed deep neural network model that can be applied to transform disparate medical data into actionable results (e.g., system configuration/settings, computer-aided diagnosis results, image enhancement, etc.).

II. Description of Examples

Example Deep Learning Network Systems

FIG. 1 is a representation of an example deep learning neural network 100. The example deep neural network (DNN) 100 includes layers 120, 140, 160, and 180. The layers 120 and 140 are connected with neural connections 130. The layers 140 and 160 are connected with neural connections 150. The layers 160 and 180 are connected with neural connections 170. Data flows forward via inputs 112, 114, 116 from the input layer 120 to the output layer 180 and to an output 190.

The layer 120 is an input layer that, in the example of FIG. 1, includes a plurality of nodes 122, 124, 126. The layers 140 and 160 are hidden layers and include, the example of FIG. 1, nodes 142, 144, 146, 148, 162, 164, 166, 168. The neural network 100 may include more or less hidden layers 140 and 160 than shown. The layer 180 is an output layer and includes, in the example of FIG. 1, a node 182 with an output 190. Each input 112-116 corresponds to a node 122-126 of the input layer 120, and each node 122-126 of the input layer 120 has a connection 130 to each node 142-148 of the hidden layer 140. Each node 142-148 of the hidden layer 140 has a connection 150 to each node 162-168 of the hidden layer 160. Each node 162-168 of the hidden layer 160 has a connection 170 to the output layer 180. The output layer 180 has an output 190 to provide an output from the example neural network 100.

Of connections 130, 150, and 170 certain example connections 132, 152, 172 may be given added weight while other example connections 134, 154, 174 may be given less weight in the neural network 100. Input nodes 122-126 are activated through receipt of input data via inputs 112-116, for example. Nodes 142-148 and 162-168 of hidden layers 140 and 160 are activated through the forward flow of data through the network 100 via the connections 130 and 150, respectively. Node 182 of the output layer 180 is activated after data processed in hidden layers 140 and 160 is sent via connections 170. When the output node 182 of the output layer 180 is activated, the node 182 outputs an appropriate value based on processing accomplished in hidden layers 140 and 160 of the neural network 100.

Figure 2:
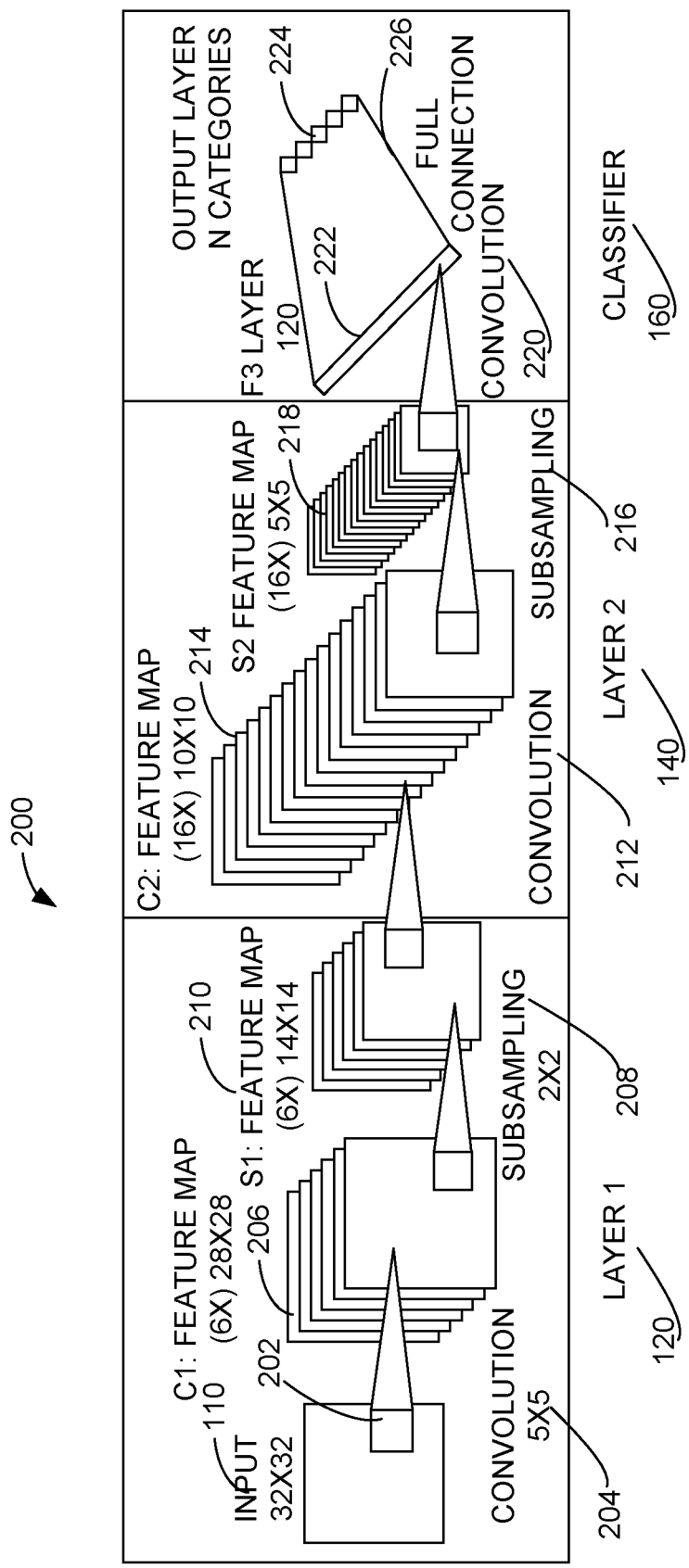
FIG. 2 illustrates a particular implementation of the example neural network as a convolutional neural network.

FIG. 2 illustrates a particular implementation of the example neural network 100 as a convolutional neural network 200. As shown in the example of FIG. 2, an input 110 is provided to the first layer 120 which processes and propagates the input 110 to the second layer 140. The input 110 is further processed in the second layer 140 and propagated to the third layer 160. The third layer 160 categorizes data to be provided to the output layer 180. More specifically, as shown in the example of FIG. 2, a convolution 204 (e.g., a 5×5 convolution, etc.) is applied to a portion or window (also referred to as a "receptive field") 202 of the input 110 (e.g., a 32×32 data input, etc.) in the first layer 120 to provide a feature map 206 (e.g., a (6×) 28×28 feature map, etc.). The convolution 204 maps the elements from the input 110 to the feature map 206. The first layer 120 also provides subsampling (e.g., 2×2 subsampling, etc.) to generate a reduced feature map 210 (e.g., a (6×) 14×14 feature map, etc.). The feature map 210 undergoes a convolution 212 and is propagated from the first layer 120 to the second layer 140, where the feature map 210 becomes an expanded feature map 214 (e.g., a (16×) 10×10 feature map, etc.). After subsampling 216 in the second layer 140, the feature map 214 becomes a reduced feature map 218 (e.g., a (16×) 4×5 feature map, etc.). The feature map 218 undergoes a convolution 220 and is propagated to the third layer 160, where the feature map 218 becomes a classification layer 222 forming an output layer of N categories 224 with connection 226 to the convoluted layer 222, for example.

Figure 3:
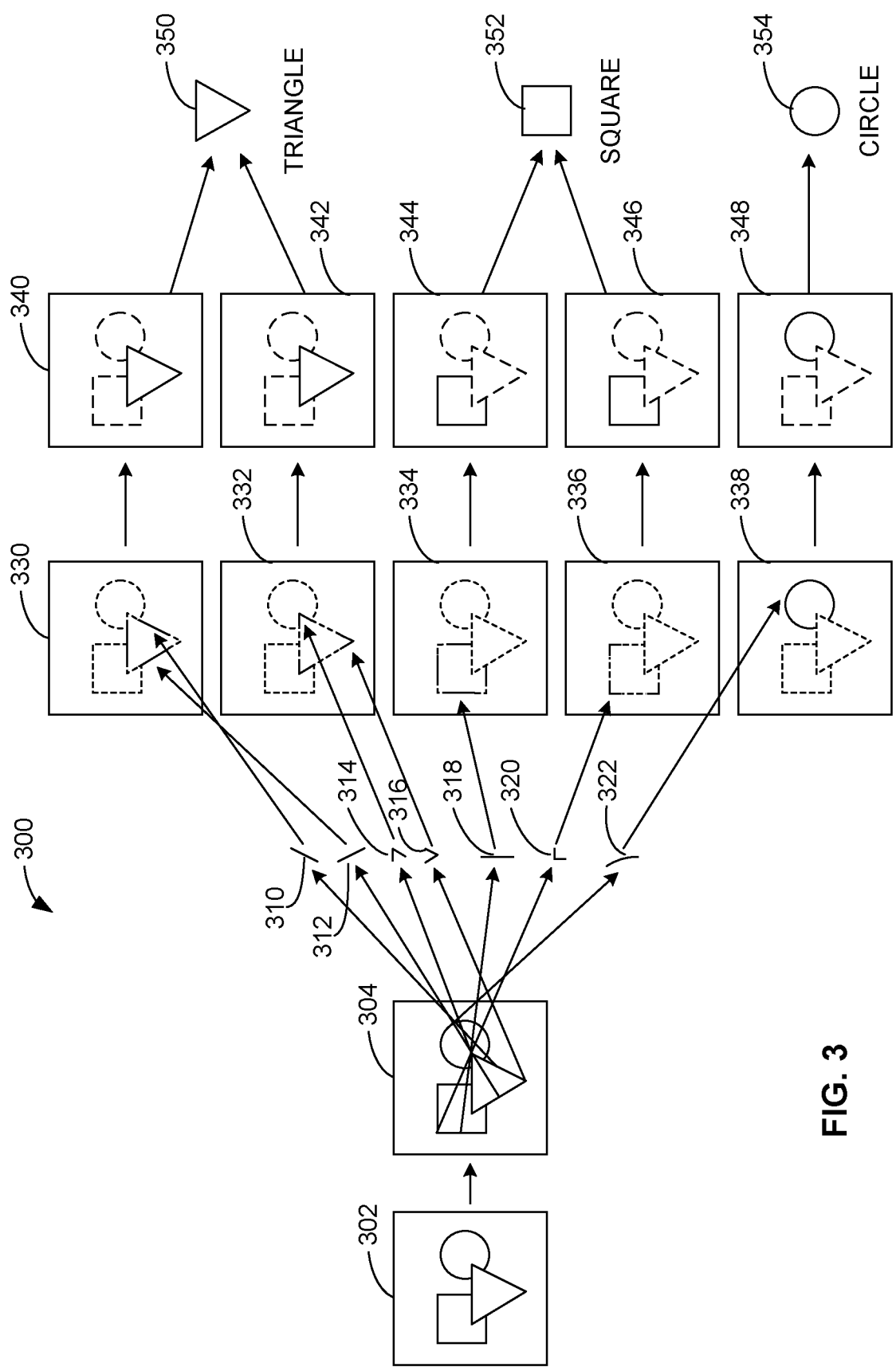
FIG. 3 is a representation of an example implementation of an image analysis convolutional neural network.

FIG. 3 is a representation of an example implementation of an image analysis convolutional neural network 300. The convolutional neural network 300 receives an input image 302 and abstracts the image in a convolution layer 304 to identify learned features 310-322. In a second convolution layer 330, the image is transformed into a plurality of images 330-338 in which the learned features 310-322 are each accentuated in a respective sub-image 330-338. The images 330-338 are further processed to focus on the features of interest 310-322 in images 340-348. The resulting images 340-348 are then processed through a pooling layer which reduces the size of the images 340-348 to isolate portions 350-354 of the images 340-348 including the features of interest 310-322. Outputs 350-354 of the convolutional neural network 300 receive values from the last non-output layer and classify the image based on the data received from the last non-output layer. In certain examples, the convolutional neural network 300 may contain many different variations of convolution layers, pooling layers, learned features, and outputs, etc.

Figure 4A:
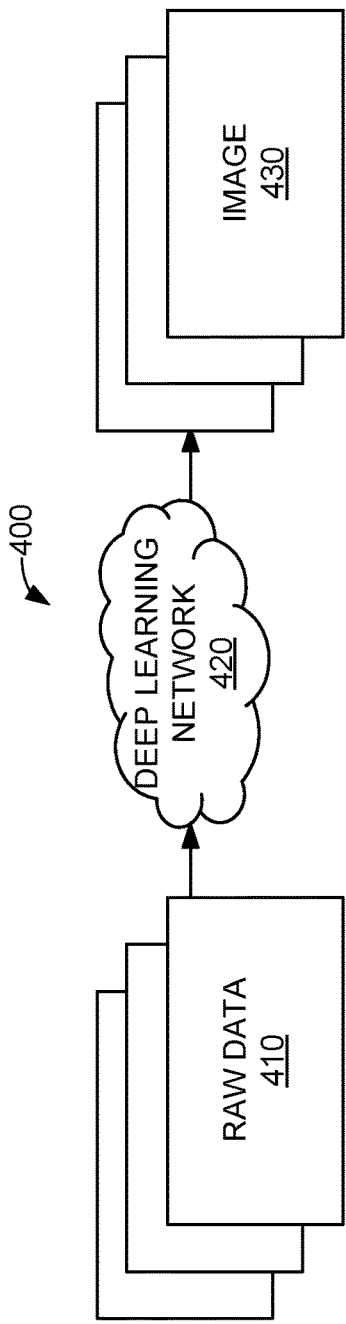
FIG. 4A illustrates an example configuration to apply a deep learning network to process and/or otherwise evaluate an image.

FIG. 4A illustrates an example configuration 400 to apply a deep learning network to process and/or otherwise evaluate an image. Deep learning can be applied to a variety of processes including image acquisition, image reconstruction, image analysis/diagnosis, etc. As shown in the example configuration 400 of FIG. 4A, raw data 410 (e.g., raw data 410 such as sonogram raw data, etc., obtained from an imaging scanner such as an x-ray, computed tomography, ultrasound, magnetic resonance, etc., scanner) is fed into a deep learning network 420. The deep learning network 420 processes the data 410 to correlate and/or otherwise combine the raw image data 420 into a resulting image 430 (e.g., a "good quality" image and/or other image providing sufficient quality for diagnosis, etc.). The deep learning network 420 includes nodes and connections (e.g., pathways) to associate raw data 410 with a finished image 430. The deep learning network 420 can be a training deep learning network that learns the connections and processes feedback to establish connections and identify patterns, for example. The deep learning network 420 can be a deployed deep learning network that is generated from a training network and leverages the connections and patterns established in the training network to take the input raw data 410 and generate the resulting image 430, for example.

Once the DLN 420 is trained and produces good images 630 from the raw image data 410, the network 420 can continue the "self-learning" process and refine its performance (e.g., accuracy, consistency, precision, etc.) as it operates. For example, there is "redundancy" in the input data (raw data) 410 and redundancy in the network 420, and the redundancy can be exploited.

If weights assigned to nodes in the DLN 420 are examined, there are likely many connections and nodes with very low weights. The low weights indicate that these connections and nodes contribute little to the overall performance of the DLN 420. Thus, these connections and nodes are redundant. Such redundancy can be evaluated to reduce redundancy in the inputs (raw data) 410. Reducing input 410 redundancy can result in savings in scanner hardware, reduced demands on components, and also reduced exposure dose to the patient, for example.

In deployment, the configuration 400 forms a package 400 including an input definition 410, a trained network 420, and an output definition 430. The package 400 can be deployed and installed with respect to another system, such as an imaging system, analysis engine, etc.

Figure 4B:
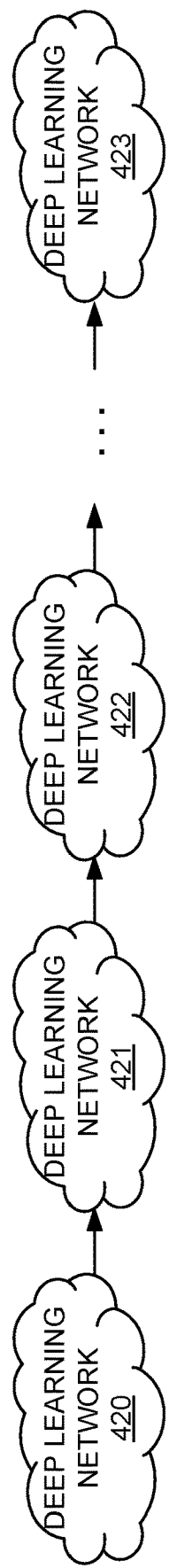
FIG. 4B illustrates a combination of a plurality of deep learning networks.

As shown in the example of FIG. 4B, the deep learning network 420 can be chained and/or otherwise combined with a plurality of deep learning networks 421-423 to form a larger learning network. The combination of networks 420-423 can be used to further refine responses to inputs and/or allocate networks 420-423 to various aspects of a system, for example.

In some examples, in operation, "weak" connections and nodes can initially be set to zero. The DLN 420 then processes its nodes in a retaining process. In certain examples, the nodes and connections that were set to zero are not allowed to change during the retraining. Given the redundancy present in the network 420, it is highly likely that equally good images will be generated. As illustrated in FIG. 4B, after retraining, the DLN 420 becomes DLN 421. DLN 421 is also examined to identify weak connections and nodes and set them to zero. This further retrained network is DLN 422. The example DLN 422 includes the "zeros" in DLN 421 and the new set of nodes and connections. The DLN 422 continues to repeat the processing until a good image quality is reached at a DLN 423, which is referred to as a "minimum viable net (MVN)". The DLN 423 is an MVN because if additional connections or nodes are attempted to be set to zero in DLN 423, image quality can suffer.

Once the MVN has been obtained with the DLN 423, "zero" regions (e.g., dark irregular regions in a graph) are mapped to the input 410. Each dark zone is likely to map to one or a set of parameters in the input space. For example, one of the zero regions may be linked to the number of views and number of channels in the raw data. Since redundancy in the network 423 corresponding to these parameters can be reduced, there is a highly likelihood that the input data can be reduced and generate equally good output. To reduce input data, new sets of raw data that correspond to the reduced parameters are obtained and run through the DLN 421. The network 420-423 may or may not be simplified, but one or more of the DLNs 420-423 is processed until a "minimum viable input (MVI)" of raw data input 410 is reached. At the MVI, a further reduction in the input raw data 410 may result in reduced image 430 quality. The MVI can result in reduced complexity in data acquisition, less demand on system components, reduced stress on patients (e.g., less breath-hold or contrast), and/or reduced dose to patients, for example.

By forcing some of the connections and nodes in the DLNs 420-423 to zero, the network 420-423 to build "collaterals" to compensate. In the process, insight into the topology of the DLN 420-423 is obtained. Note that DLN 421 and DLN 422, for example, have different topology since some nodes and/or connections have been forced to zero. This process of effectively removing connections and nodes from the network extends beyond "deep learning" and can be referred to as "deep-deep learning".

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 5:
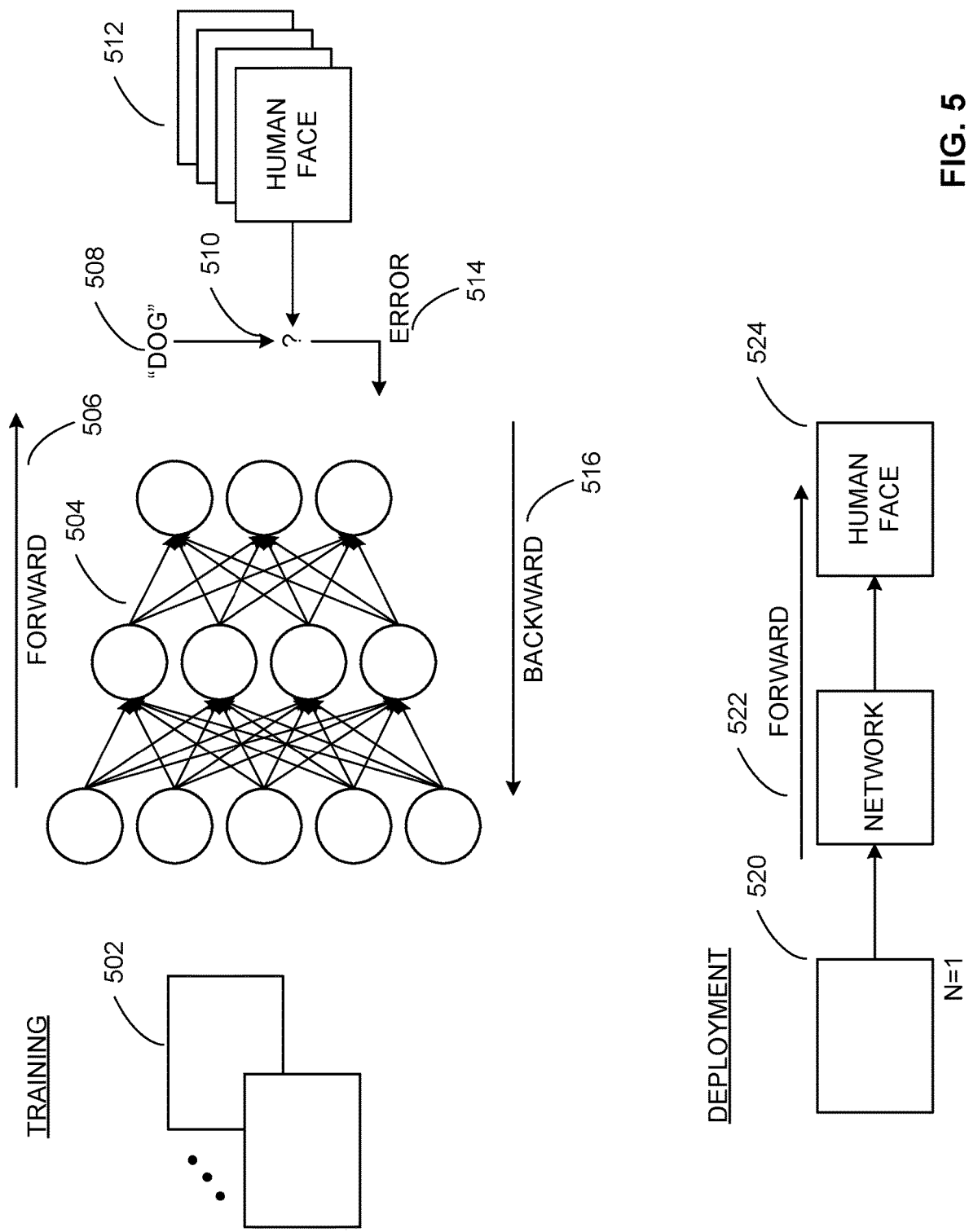
FIG. 5 illustrates example training and deployment phases of a deep learning network.

FIG. 5 illustrates example training and deployment phases of a deep learning network. As shown in the example of FIG. 5, in the training phase, a set of inputs 502 is provided to a network 504 for processing. In this example, the set of inputs 502 can include facial features of an image to be identified. The network 504 processes the input 502 in a forward direction 506 to associate data elements and identify patterns. The network 504 determines that the input 502 represents a dog 508. In training, the network result 508 is compared 510 to a known outcome 512. In this example, the known outcome 512 is a human face (e.g., the input data set 502 represents a human face, not a dog face). Since the determination 508 of the network 504 does not match 510 the known outcome 512, an error 514 is generated. The error 514 triggers an analysis of the known outcome 512 and associated data 502 in reverse along a backward pass 516 through the network 504. Thus, the training network 504 learns from forward 506 and backward 516 passes with data 502, 512 through the network 405.

Once the comparison of network output 508 to known output 512 matches 510 according to a certain criterion or threshold (e.g., matches n times, matches greater than x percent, etc.), the training network 504 can be used to generate a network for deployment with an external system. Once deployed, a single input 520 is provided to a deployed deep learning network 522 to generate an output 524. In this case, based on the training network 504, the deployed network 522 determines that the input 520 is an image of a human face 524.

Figure 6:
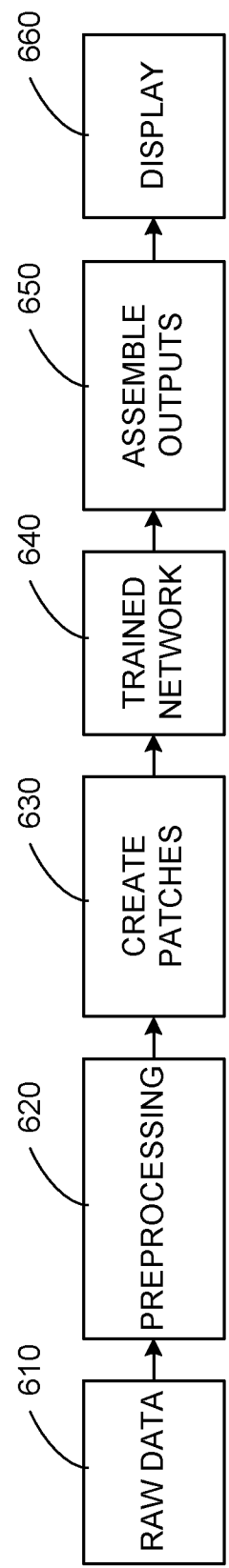
FIG. 6 illustrates an example product leveraging a trained network package to provide a deep learning product offering.

FIG. 6 illustrates an example product leveraging a trained network package to provide a deep learning product offering. As shown in the example of FIG. 6, an input 610 (e.g., raw data) is provided for preprocessing 620. For example, the raw input data 610 is preprocessed 620 to check format, completeness, etc. Once the data 610 has been preprocessed 620, patches are created 630 of the data. For example, patches or portions or "chunks" of data are created 630 with a certain size and format for processing. The patches are then fed into a trained network 640 for processing. Based on learned patterns, nodes, and connections, the trained network 640 determines outputs based on the input patches. The outputs are assembled 650 (e.g., combined and/or otherwise grouped together to generate a usable output, etc.). The output is then displayed 660 and/or otherwise output to a user (e.g., a human user, a clinical system, an imaging modality, a data storage (e.g., cloud storage, local storage, edge device, etc.), etc.).

Figure 7A:
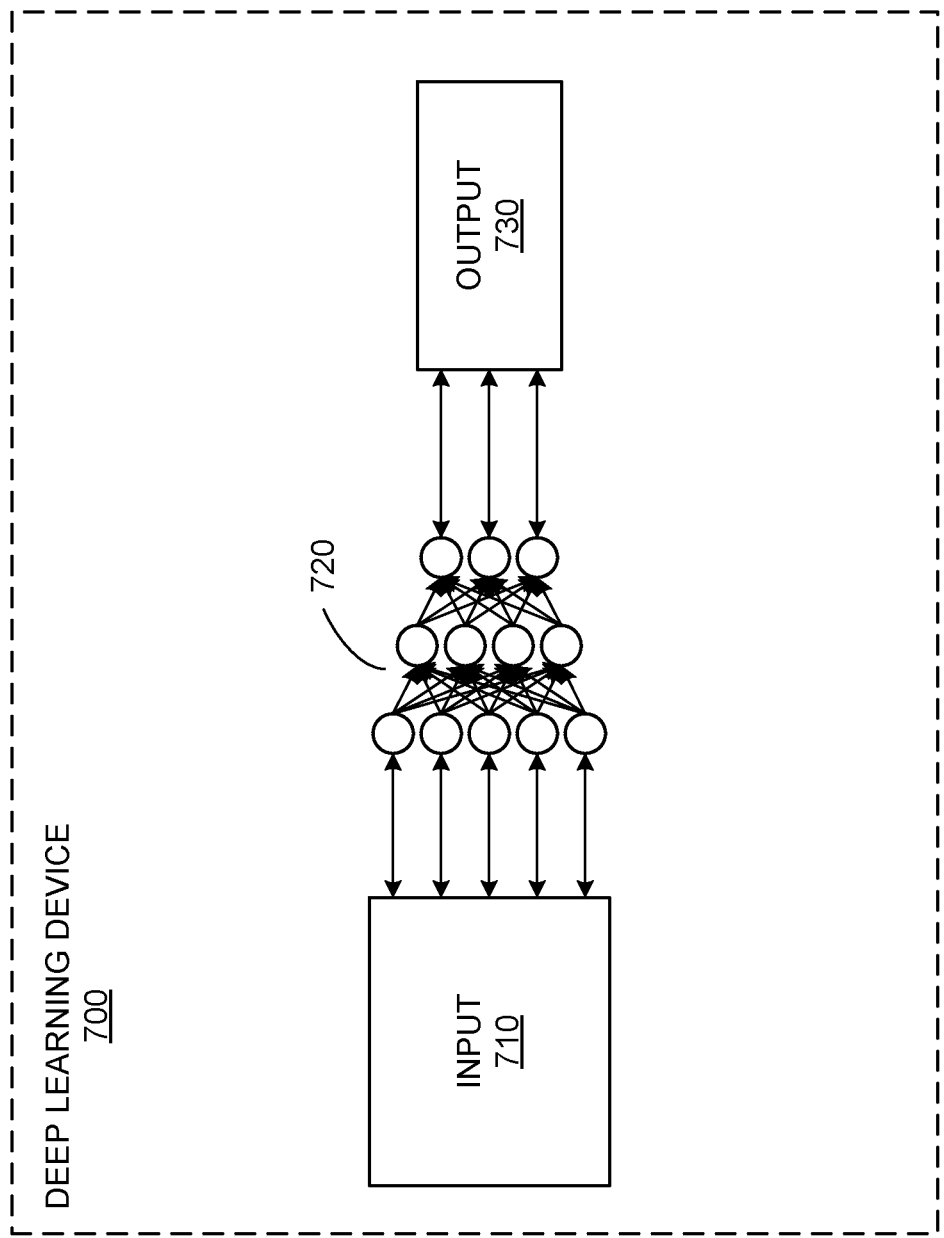
FIGS. 7A-7C illustrate various deep learning device configurations.
Figure 7B:
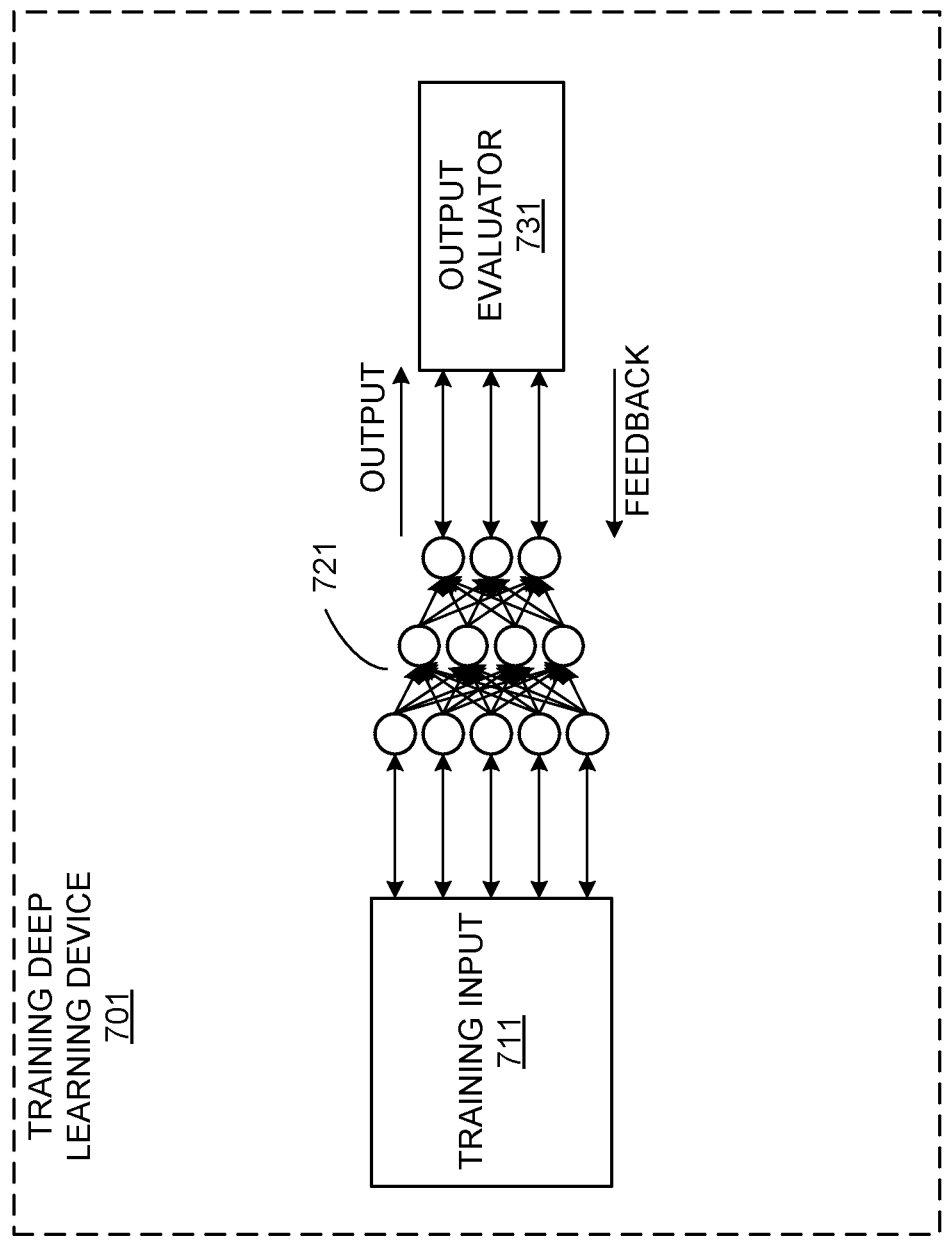
Figure 7C:
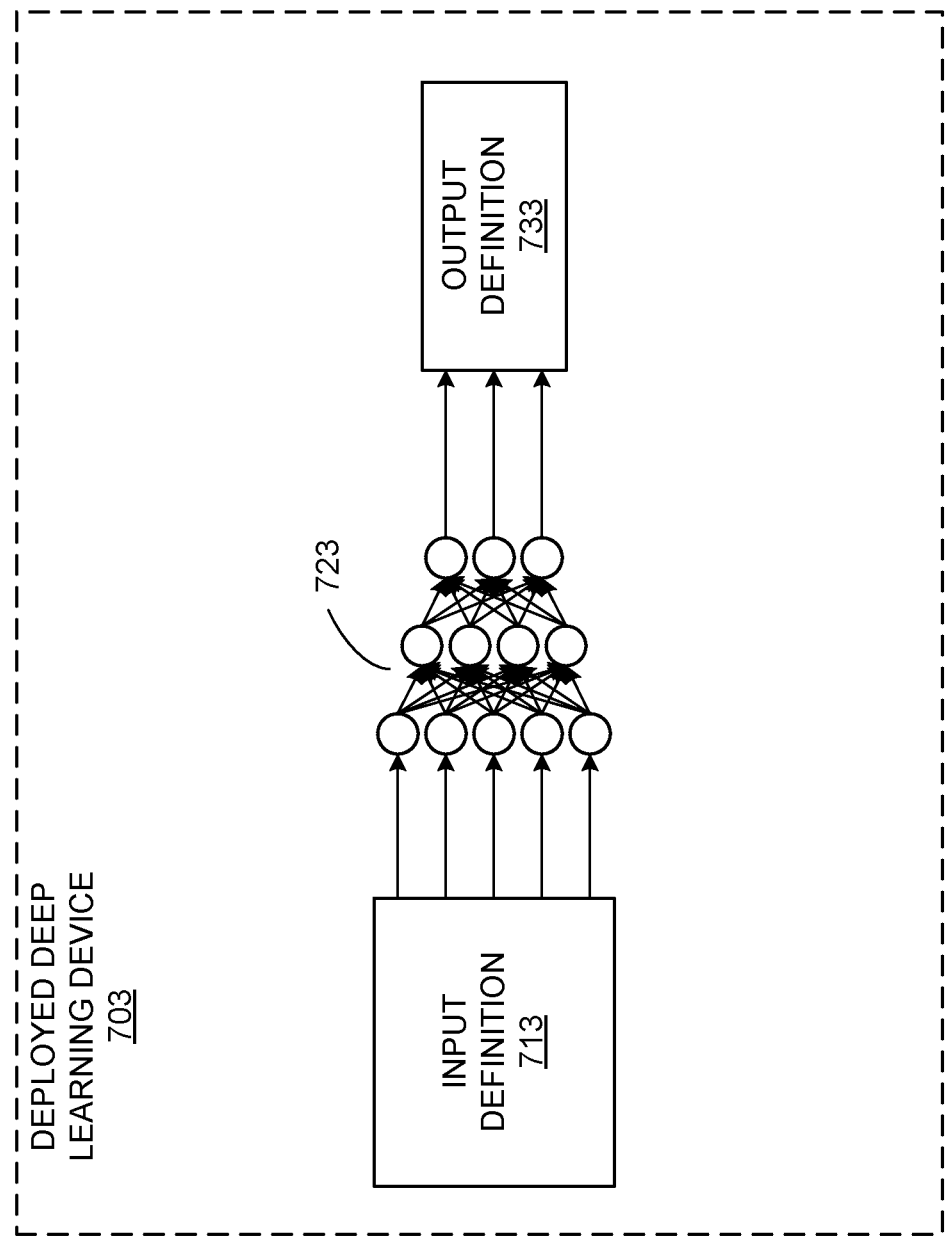

As discussed above, deep learning networks can be packaged as devices for training, deployment, and application to a variety of systems. FIGS. 7A-7C illustrate various deep learning device configurations. For example, FIG. 7A shows a general deep learning device 700. The example device 700 includes an input definition 710, a deep learning network model 720, and an output definitions 730. The input definition 710 can include one or more inputs translating into one or more outputs 730 via the network 720.

FIG. 7B shows an example training deep learning network device 701. That is, the training device 701 is an example of the device 700 configured as a training deep learning network device. In the example of FIG. 7B, a plurality of training inputs 711 are provided to a network 721 to develop connections in the network 721 and provide an output to be evaluated by an output evaluator 731. Feedback is then provided by the output evaluator 731 into the network 721 to further develop (e.g., train) the network 721. Additional input 711 can be provided to the network 721 until the output evaluator 731 determines that the network 721 is trained (e.g., the output has satisfied a known correlation of input to output according to a certain threshold, margin of error, etc.).

FIG. 7C depicts an example deployed deep learning network device 703. Once the training device 701 has learned to a requisite level, the training device 701 can be deployed for use. While the training device 701 processes multiple inputs to learn, the deployed device 703 processes a single input to determine an output, for example. As shown in the example of FIG. 7C, the deployed device 703 includes an input definition 713, a trained network 723, and an output definition 733. The trained network 723 can be generated from the network 721 once the network 721 has been sufficiently trained, for example. The deployed device 703 receives a system input 713 and processes the input 713 via the network 723 to generate an output 733, which can then be used by a system with which the deployed device 703 has been associated, for example.

Example Artificial Intelligence Modeling Systems and Methods

An Artificial Intelligence model (A.I. model) must see a variety of features during its training so that the model can understand its underlying representation and model a function from given input data to an output prediction.

In healthcare, each patient and their medical condition(s) are different from the rest of the population. Many variables play a vital role in characterizing the patient, such as medical history, family history, daily activity, work environment, etc. During the A.I. model training, an A.I. model, such as a CNN and/or other deep learning network, is to map from input data to output data through a learned function. De-identified data collected and approved for research purposes can be used to learn this mapping function, for example. For at least this reason, patient data collection is a first and important action to train the A.I. model, followed by data annotation. Also, this training usually happens on high-performance computing devices.

Figure 8:
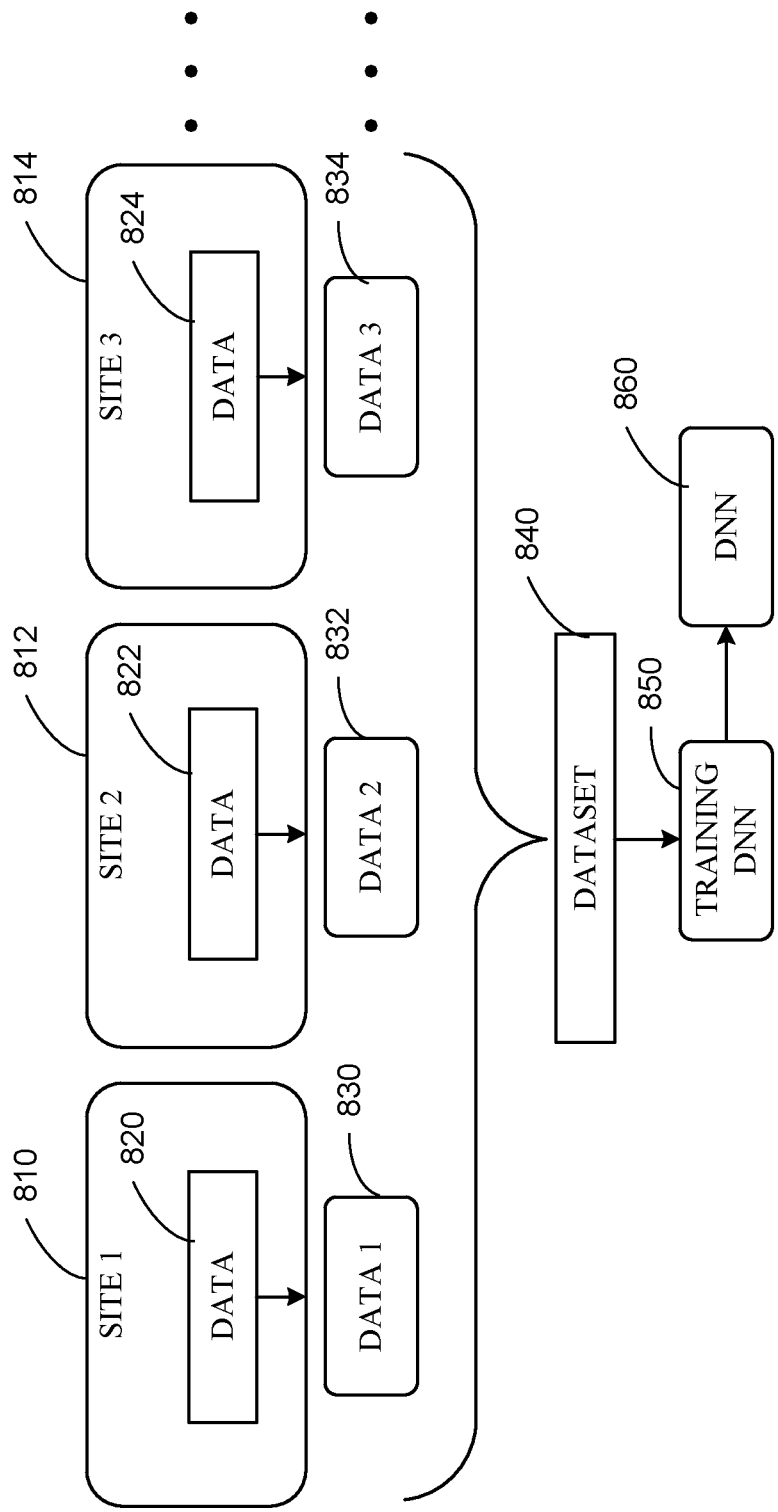
FIGS. 8-10 depict example environments to generate data to train a deep neural network.

Practically, the best way to train the A.I. model is to collect all data from different sites and train a deep neural network (DNN) outside the sites on an aggregated dataset such as shown in the example of FIG. 8. For example, sites 810-814 include data 820-824 from which a sample 830-834 is extracted to form a dataset 840. The dataset 840 is provided to a training deep neural network (DNN) 850. Once the training DNN 850 is trained using the dataset 840, a resulting DNN model 860 can be deployed.

However, due to legal and regulatory restrictions, there are sites and/or regions where the data cannot leave the premises. Such restrictions prevent the A.I. model from learning site/region specific medical conditions, and, as a result of the deficiency in training data, the A.I. model will not be able to predict outcomes successfully.

To deploy a reliable A.I. model that can predict a specific medical condition is critical from an efficiency perspective as well as from a business perspective. Therefore, in contrast to prior approaches, certain examples provide a solution that can fulfill the goal of building global and scalable A.I. products while respecting legal and regulatory restrictions on data and protecting patient privacy.

Figure 9:
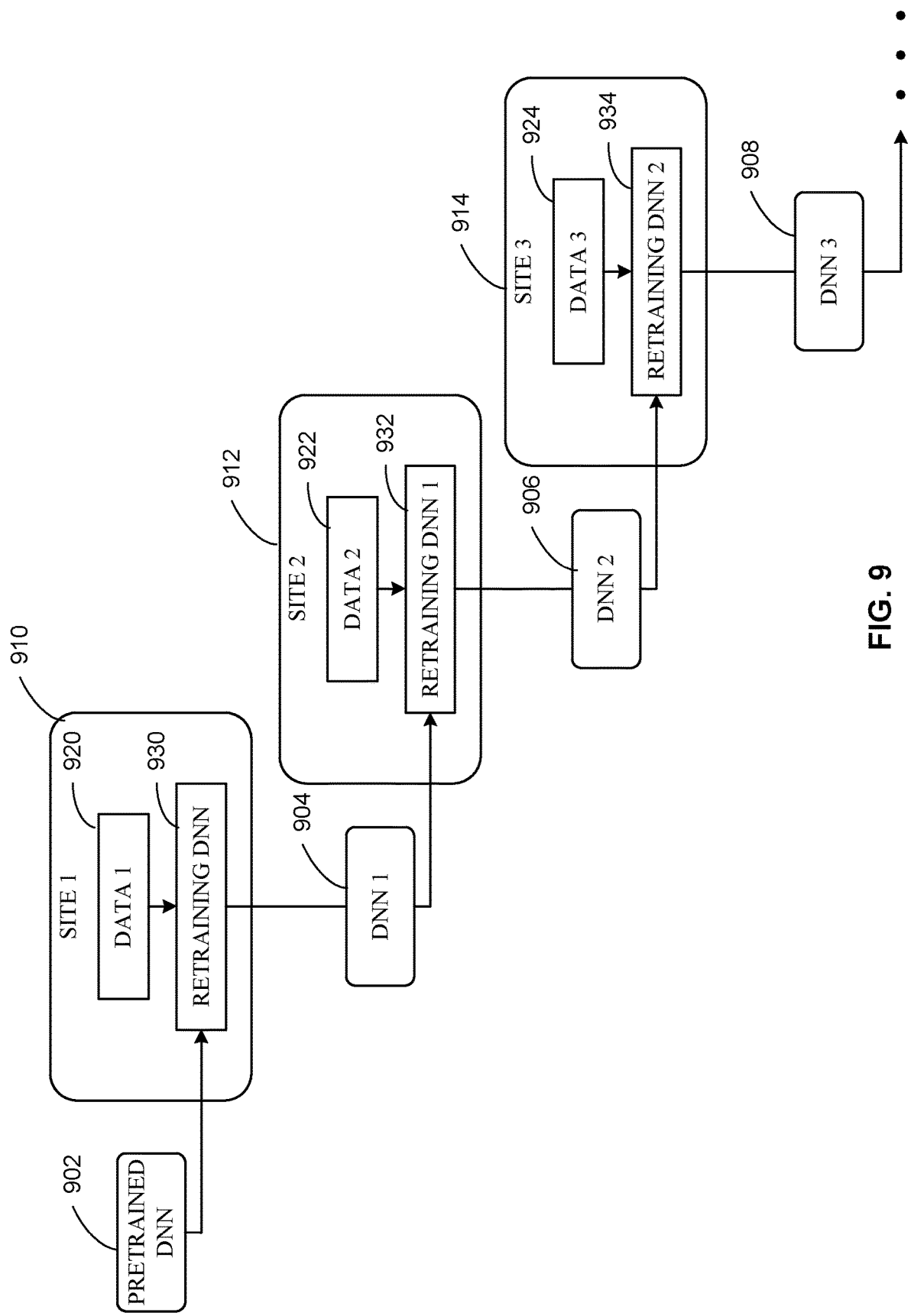

One approach to a scalable solution is to train/retrain one A.I. model for each medical condition at every site in a sequence as shown in FIG. 9. For example, as shown in FIG. 9, a pretrained DNN 902 is provided to a first site 910, which uses its data 920 to retrain 930 the DNN to produce a first DNN model 904. The retrained DNN model 904 is provided to a second site 912, which uses its data 922 to retrain 932 the DNN 904 to produce a second DNN model 906. The retrained DNN model 906 is provided to a third site 914, which uses its data 924 to retrain 934 the DNN 906 to produce a third DNN model 908. This process of site-based retraining can be repeated for one or more sites that have data available for retraining the network and/or until a certain reliability/accuracy threshold is reached, for example.

Thus, the model trained at a first site using that site's region-specific patient data can be retrained at a second site. This process can be repeated at N number of sites. However, these A.I. models suffer from a problem called catastrophic forgetting. With catastrophic forgetting, once an A.I. model is trained to do a specific task at the first site (e.g., pneumothorax classification, etc.), the model cannot easily be trained to do new tasks or the same task at a different site (e.g., incrementally learning to recognize other pneumothorax features from data at the rest of the sites, etc.). These fine-grained features must be learned throughout the sites for a scalable A.I. solution, and catastrophic forgetting can prevent this cross-site learning from occurring. Thus, this approach fails to train the network on a variety of data and also suffers from limited generalizability. As described further below, certain examples alleviate this problem and produce a single efficient A.I. model per medical condition by taking all features from all the regions into account under compliance.

Figure 10:
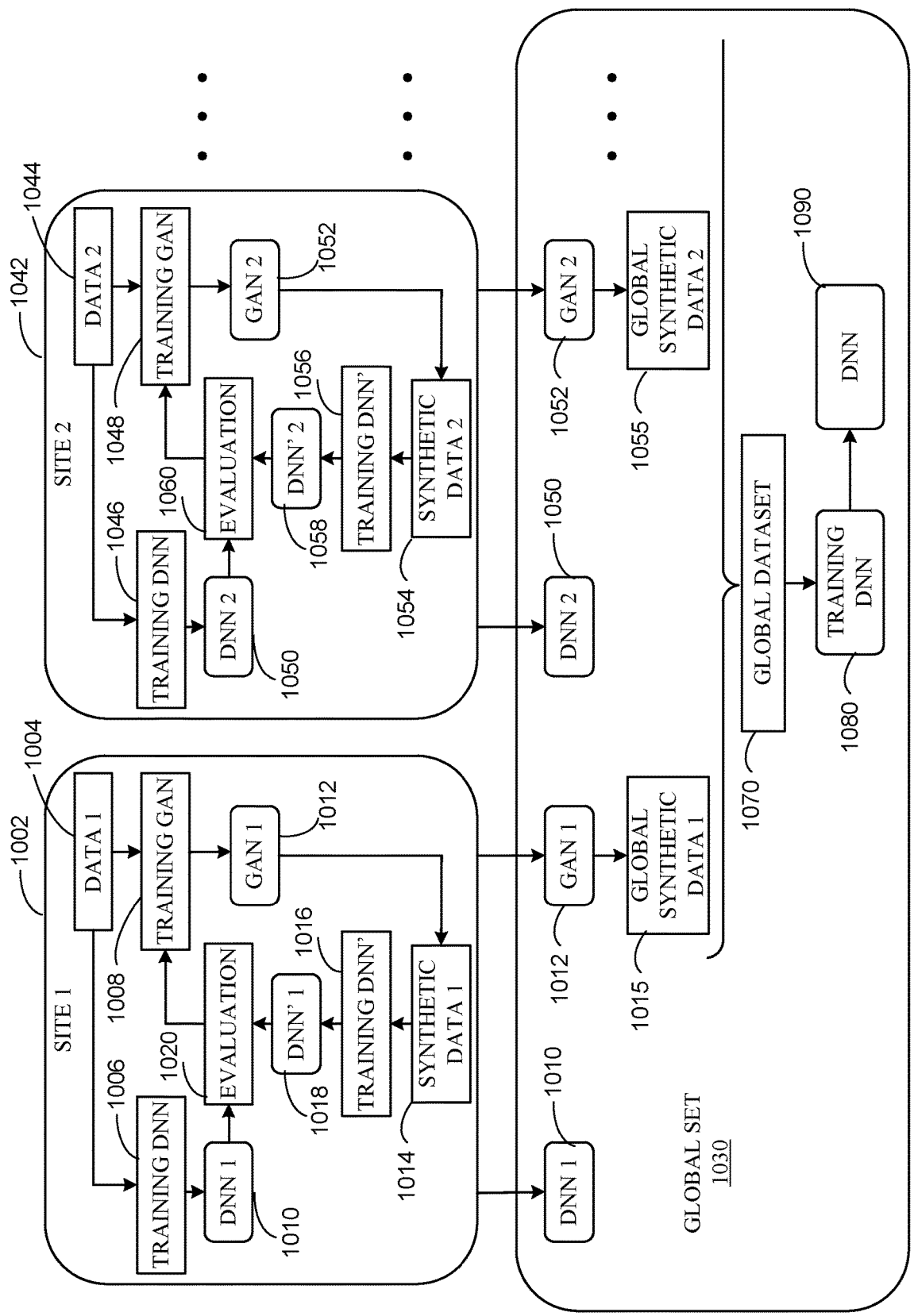

Certain examples include a two-step solution reflected in the block diagram of FIG. 10. First, one or more Generative Adversarial Networks (hereinafter referred to as 'GANs' or 'A.I. GAN model') are trained at participating sites. DNN(s) are also trained using real data at each site. Generated images are evaluated by training a local DNN using synthetic data and comparing performance of the A.I. GAN model with the output of the trained local DNN. Performance can be measured by comparing the outputs to determine accuracy, precision, consistency, etc., between the models, for example. Based on the results, a system can continue or retrain an A.I. GAN algorithm to produce a more robust GAN data generator model.

Next, the trained GAN models are used to generate synthetic data that is utilized later to train one global A.I. model per medical condition. For example, compliant global data can be generated by leveraging regional data generators. This novel approach provides an internal fine-grained representation of each site's data through synthetic data that is generated outside in compliance with data privacy and other regulations. The result is a master A.I. model that can predict comparatively better than other models as this A.I. model will have seen all site-specific feature representations within synthetically generated training images.

Once the global A.I. model is trained, the model can be evaluated on real data that has been deidentified and approved globally. Scientifically, these generated images are known to follow the distribution of training set (e.g., "real" medical images), so the generated images tend to represent medical conditions associated with patients of that specific site. Therefore, the A.I. GAN model can be seen as a mathematical function of site-specific features to produce medical data outside the site premises while protecting the site's compliance with data and patient privacy regulations, etc.

For example, synthetic data can be generated at a healthcare provider's site, and interaction between real data training and synthetic data training can be facilitated to produce secure, legal, HIPAA-compliant A.I. models. A.I. models can be generated using a combination of real data and synthetic data using a particular sequence. First, a network is trained on real data to obtain a first trained network for a clinical purpose. Next, a network is trained on synthetic data to obtain a second trained network, wherein the synthetic data is derived from the real data. Performance of the first trained network and the second trained network are evaluated to determine, based on the evaluation, whether more real data should be used to create additional synthetic data. Performance can be measured by comparing the outputs of the network models to determine accuracy, precision, consistency, etc., between the models, for example. If additional synthetic data is warranted or desired, then additional real data can be gathered to generate additional synthetic data by training a neural network and/or other A.I. model with the additional real data. If no additional data is warranted or desired, then, the first and second trained networks can be extracted and deployed as a module from the site. This sequence of actions can be repeated in other sites, and the deployed, trained networks can be centralized for deployment and use, for example.

Thus, synthetic data can be generated and aggregated from all the generative models, which are collected from different sites. The aggregated synthetic data can be used to train a deep neural network, which can be deployed and applied to a variety of medical imaging and/or other clinical problems such as image quality, computer-aided diagnosis, imaging system configuration, image data processing, etc.

As shown in the example of FIG. 10, at a first site 1002, data 1004 is provided to a trainer 1006, 1008 to train both a DNN 1010 and a GAN 1012. Once the GAN 1012 is trained, the GAN 1012 can be used to generate synthetic data 1014. The synthetic data 1014 can be used by a trainer 1016 to train another DNN (DNN') 1018. An evaluator 1020 compares the DNN 1010 trained with the real data 1004 with the DNN' 1018 trained with the synthetic data 1014. For example, the evaluator 1020 can compare similarity/difference in performance (e.g., accuracy, precision, consistency, etc.) between the DNN 1010 and the DNN' 1018, and/or other evaluation metric such as accuracy, dice score, area under curve (AUC), etc. The evaluator 1020 determines whether more real data 1004 is to be used to create additional synthetic data 1014. If more synthetic data 1014 is to be created, then real data 1004 is again used by the trainer 1008 to train the GAN 1012, which provides additional synthetic data 1014. If no additional synthetic data 1014 is to be created, the DNN 1010 and the GAN 1012 are provided, along with the synthetic data 1014, to a global set 1030.

Similarly, at a second site 1042, data 1044 is provided to a trainer 1046, 1048 to train both a DNN 1050 and a GAN 1052. Once the GAN 1052 is trained, the GAN 1052 can be used to generate synthetic data 1054. The synthetic data 1054 can be used by a trainer 1056 to train another DNN (DNN') 1058. An evaluator 1060 compares the DNN 1050 trained with the real data 1044 with the DNN' 1058 trained with the synthetic data 1054. The evaluator 1020 determines whether more real data 1044 is to be used to create additional synthetic data 1054. If more synthetic data 1044 is to be created, then real data 1044 is again used by the trainer 1048 to train the GAN 1042, which provides additional synthetic data 1054. If no additional synthetic data 1044 is to be created, the DNN 1050 and the GAN 1052 are provided, along with the synthetic data 1044, to the global set 1030. Such synthetic data generation can be replicated across multiple sites and provided to the global set 1030 to form a dataset 1070.

In certain examples, the dataset 1070 is used by a trainer 1080 to train a DNN 1090 of the global set 1030. Thus, a DNN model 1090 can be formed from synthetic data 1014, 1054 generated from real data 1004, 1044 from a plurality of sites 1002, 1042 using DNN 1010, 1018, 1050, 1058 and GAN 1012, 1052 models providing a large dataset 1070 to robustly train 1080 the ultimate deep learning network model 1090. The network model 1090 can be deployed and applied to a variety of clinical situations such as image system configuration, image quality management, image data processing, patient analytics, computer aided diagnosis, etc.

Figure 11:
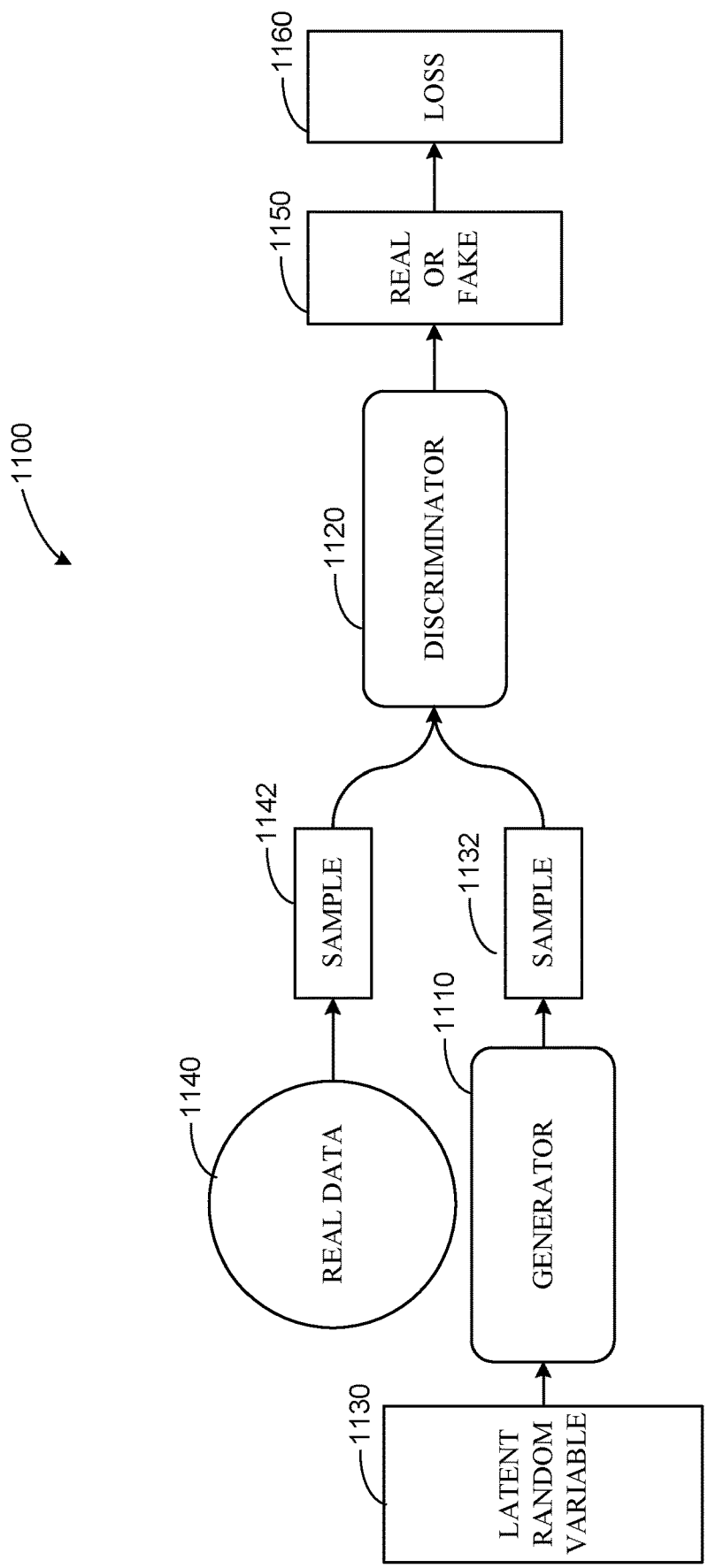
FIG. 11 shows elements of an example Generative Adversarial Network architecture.

In certain examples, a GAN includes two networks: a generator network and a discriminator (also referred to as a critic) network. The generator network produces a sample, such as an image, from a latent code (e.g., an output of an encoder of the GAN that maps an image to a corresponding code, etc.), and a distribution of these images can be indistinguishable from a training distribution. Since it is generally infeasible to engineer a function to determine whether the generator network distribution is indistinguishable from a training distribution, the discriminator network is trained to do the assessment of the generator network distribution. Since networks are differentiable, a gradient can be generated to steer both networks to the right direction. In certain examples, the generator is of main interest; the discriminator is an adaptive loss function that gets discarded once the generator has been trained. FIG. 11 shows elements of an example GAN architecture 1100. In certain examples, high-quality synthetic images can be generated by the example GAN architecture 1100 using one or more GAN algorithms such as a progressively growing GAN algorithm (e.g., by Nvidia, etc.), etc.

The example GAN architecture 1100 shown in FIG. 11 includes a generator 1110 and a discriminator 1120. The example generator 1110 (e.g., generator neural network) receives a latent random variable 1130 and produces a first sample 1132 (e.g., a first image, etc.) by processing the latent random variable 1130. Real or actual data 1140 can provide a second sample 1142 (e.g., a second image, etc.), and the real data sample 1142 and generator sample 1132 are processed by the discriminator 1120 to determine whether or not the sample image data 1132 is real or fake 1150 compared to the actual image sample 1142. Based on the outcome 1150 determined by the discriminator 1120, a loss 1160 can be determined. For example, if the discriminator 1120 sees a difference (e.g., fake) between the real image sample 1142 and the synthetic image sample 1132, then a loss 1160 in synthetic data quality through the generator 1110 can be determined. Such loss or error 1160 (e.g., in the form of a gradient or other adaptive loss function, etc.) can be used to generate additional synthetic data, adjust operation of the generator 1110, etc.

Figure 12:
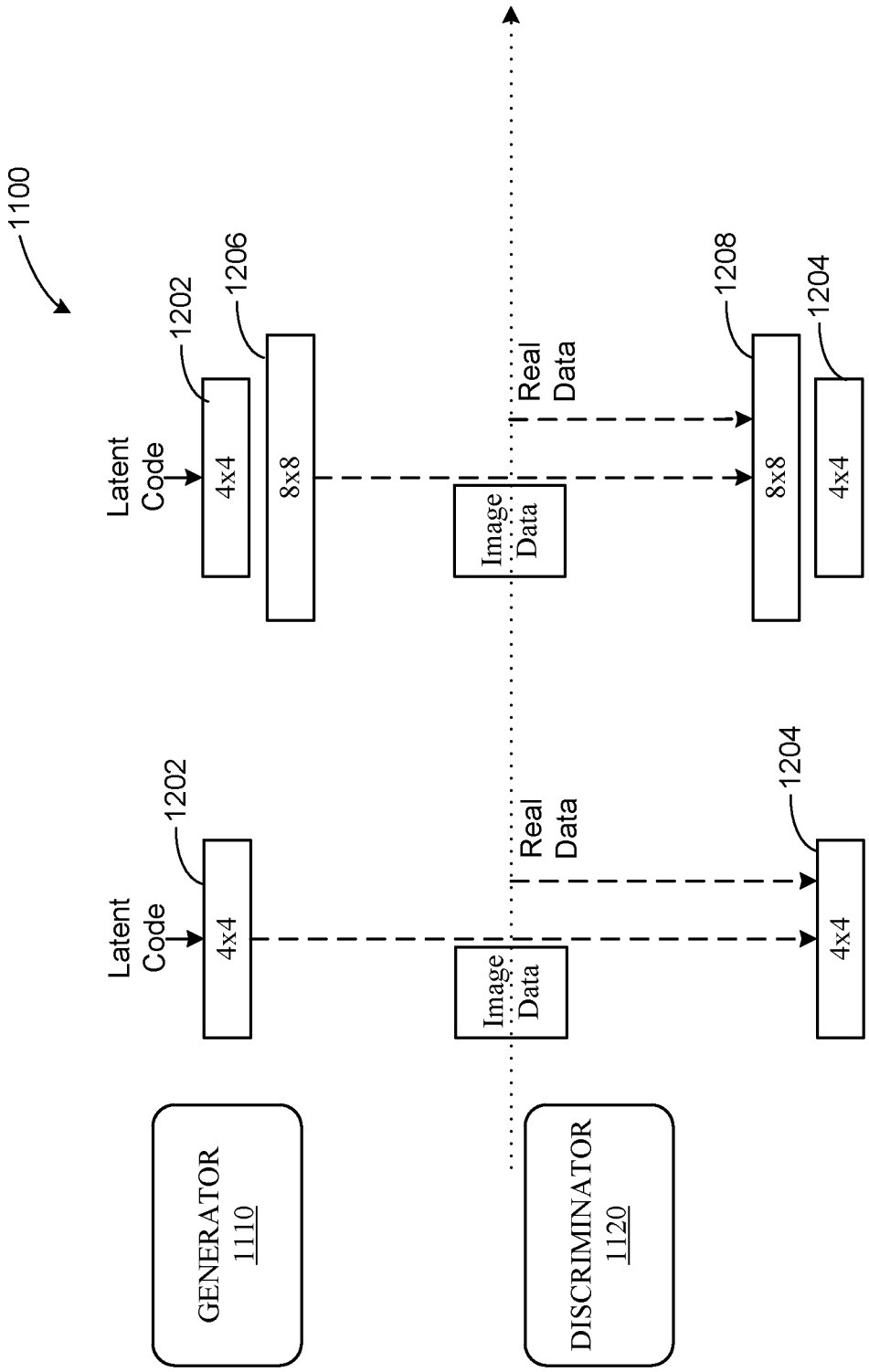
FIG. 12 shows an example of layers in the architecture of FIG. 11.

FIG. 12 shows an example of layers in the GAN 1100 separated by generator 1110 and discriminator 1120. Training can begin with a single layer 1202, 1204 in both the generator 1110 and the discriminator 1120, and layers 1206, 1208 can be incrementally added to both networks 1110, 1120 as training continues. For example, additional convolutional layers can be added to increase spatial resolution of processed images until a desired resolution is reached in the output.

Certain examples, such as shown in FIG. 10, generate robust and validated synthetic data to avoid invalid correlations and/or other failures stemming from inadequate data resulting in improper, inaccurate networks which can lead to failures threatening patient health and safety, etc. Certain examples avoid catastrophic forgetting which limits capabilities of neural networks. Certain examples train one A.I. model per medical condition using synthetic data generated outside a given site, and that model can be applied globally for that medical condition, etc. Thus, global, scalable A.I. models can be generated and deployed for applications such as imaging, clinical care, radiopharmaceutical generation, etc. The A.I. models can implement algorithms to be deployed on medical devices to achieve precision healthcare for patients, for example.

Thus, for a deep learning task, data can be divided into a plurality of groups, and GANs can be trained on the data. A global network can then be trained on the data generated by the GANs. Compared to a network trained only on native data, the global, GAN-driven network trained on synthetic data or a combination of real and synthetic data (e.g., a 1:1 combination, etc.) can provide better performance compared to a network trained only using real data.

In certain examples, a GAN generates synthetic data based on one or more random number floating point vectors between 0 and 1, even with training based on real data. Using the synthetic data generator, an infinite number of images can be generated. These images are realistic but do not resemble any of the actual images used in the training. Thus, actual patient data can be used to generate realistic synthetic data that does not correspond to the actual patient data. Patient privacy and security can be protected while providing realistic, synthetic data to train the A.I. models.

Figure 13A:
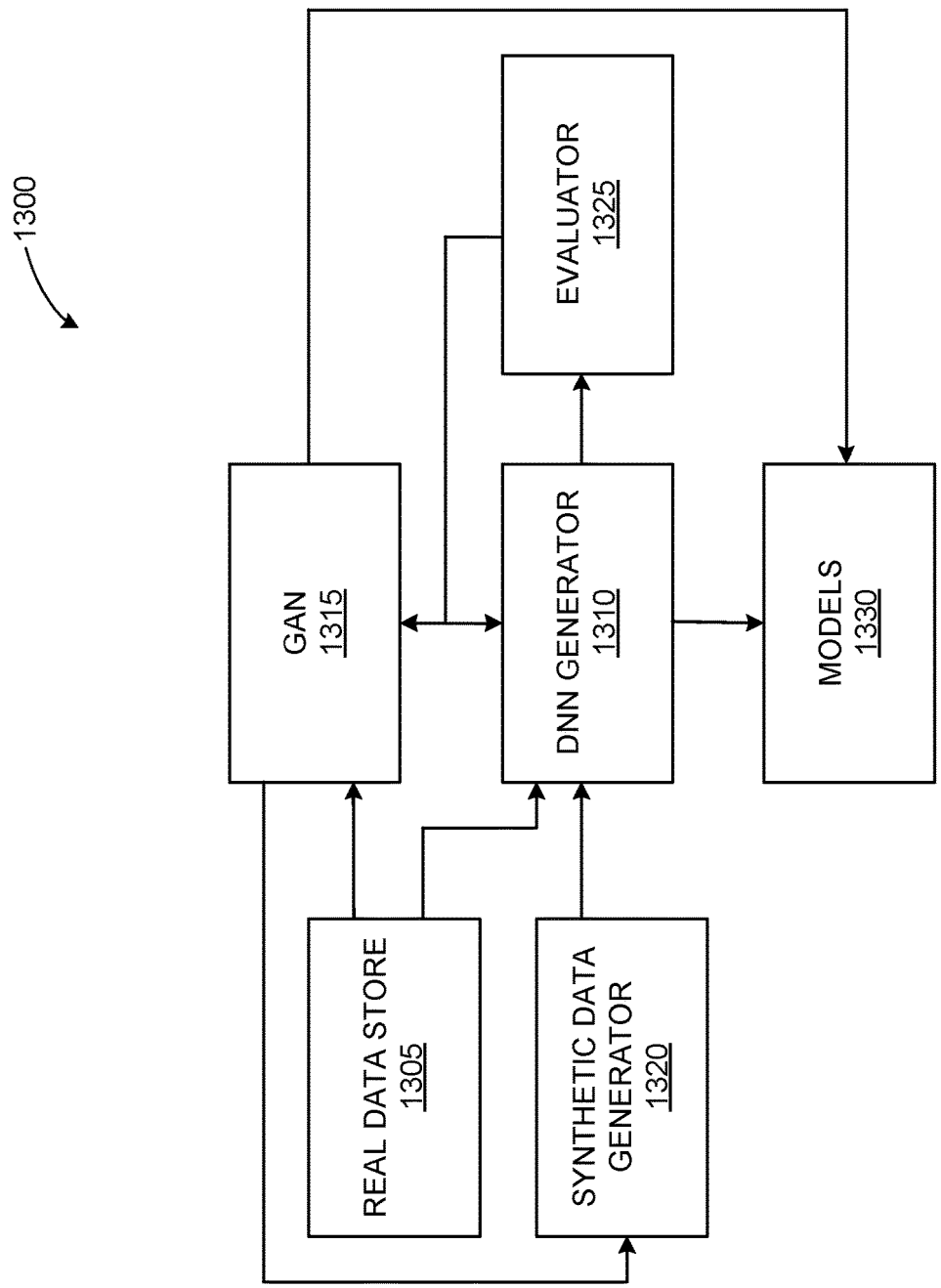
FIGS. 13A-13B illustrate example artificial intelligence model generation and data aggregation systems to generate and deploy an artificial intelligence model using a combination of real and synthetic data.

FIG. 13A illustrates an example A.I model generation system 1300 to generate and deploy an A.I. model using a combination of real and synthetic data. The example system 1300 includes a real data store 1305, a DNN generator 1310, a GAN 1315, a synthetic data generator 1320, an evaluator 1325, and one or more deployable A.I. models 1330.

The example real data store 1305 gathers real data from one or more sites to train one or more A.I. models. In certain examples, real data cannot be exported from a given site (e.g., for privacy reasons, legal requirements, etc.), so the real data store 1305 can include sub-units at individual sites instead of or in addition to a centralized real data store 1305. The real data store 1305 provides data to the DNN generator 1310, which generates, trains, and tests a DNN and/or deep learning network using the real data.

The example DNN generator 1310 develops the DNN model and provides the model to the evaluator 1325, which tests the model to evaluate its performance (e.g., accuracy, precision, consistency, etc.) and/or other similarity to another DNN model, etc. The DNN generator 1310 can trigger regeneration of the DNN model based on feedback, instruction, etc., from the evaluator 1325. In certain examples, the evaluator 1325 can compare two or more DNN models to determine whether the output of each DNN model matches, is within a margin of error/standard deviation/tolerance, etc. If the evaluator 1325 determines that the DNN models do not match (e.g., exactly or within the margin of error, etc.), then evaluator 1325 can trigger further training, model development, etc. If the models match (e.g., exactly or within the margin of error, etc.), then the evaluator 1325 can trigger finalization of the DNN and deployment of the DNN model, aggregated data set(s), etc.

Real data from the real data store 1305 is also used by the GAN 1315 to develop and train a GAN model and provide the GAN model to produce synthetic data with the synthetic data generator 1320. For example, an output of a GAN model 1315 is synthetic data that can be used by the synthetic data generator 1320 to provide further data input to the DNN generator 1310. Thus, in an absence of sufficient real data to train a deployable A.I. model, the GAN 1315 can be used to generate synthetic data with the synthetic data generator 1320 to enable to the DNN generator 1310 to train DNN models with a larger, more robust data set, formed from real and synthetic data, than would otherwise be available for a site and/or group of sites. Synthetic data can be provided by the synthetic data generator 1320 to the DNN generator 1310.

Thus, the DNN generator 131 can be repeatedly engaged to generate DNN models that can be compared to other DNN models and/or otherwise analyzed by the evaluator 1325 to determine when the DNN generator 1310 has a robust data set to train a DNN model within a set margin of error. At that point, the A.I. models (e.g., a GAN and a DNN) can be deployed to be used in an application, system, etc. For example, a DNN model and a GAN can be deployed to generate data for the global set 1030. The DNN model can also be deployed for use in configuring settings of an imaging system, processing image data (e.g., to improve image quality, for computer-aided diagnosis, etc.), processing non-image medical data (e.g., prostate exam data, vitals, laboratory results, etc., to improve data quality, for computer-aided diagnosis, etc.), etc.

Figure 13B:
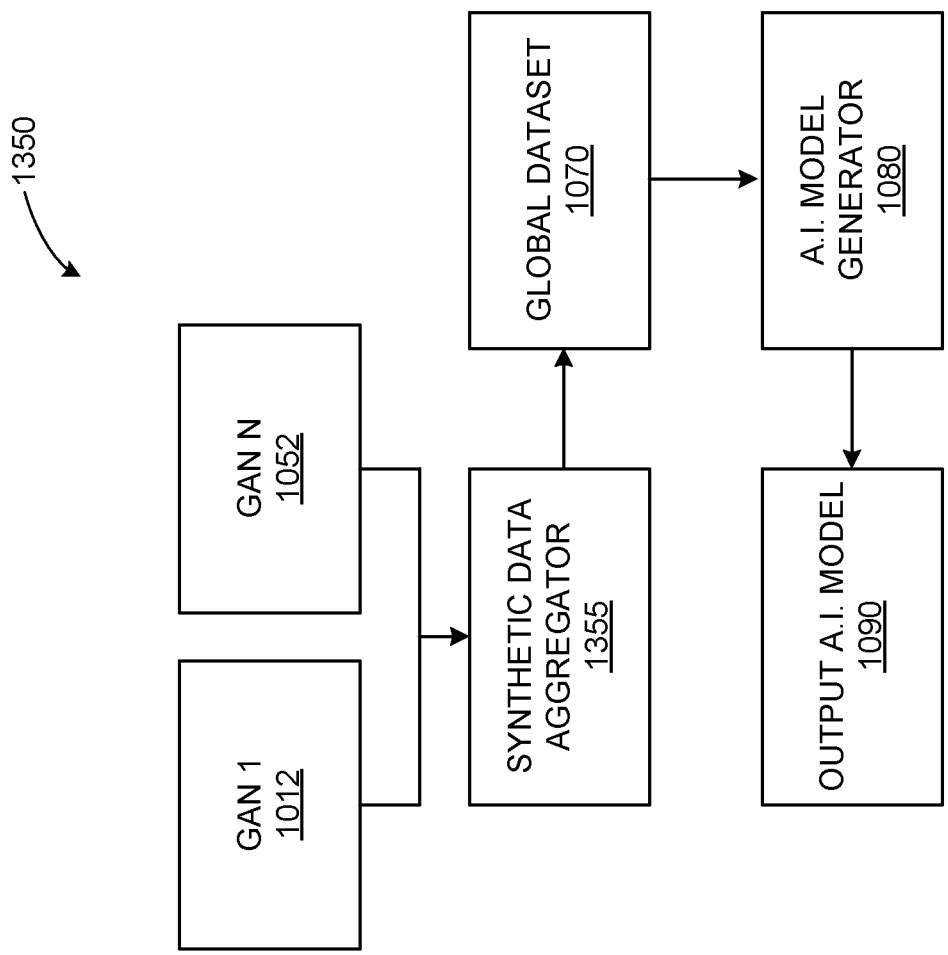

Thus, an A.I model generation system 1300 located at each site can provide GAN 1315 and DNN 1310 models to generate data for the global set 1030. FIG. 13B shows an example synthetic data aggregation system 1350 to generate the global dataset 1070 and output A.I. model 1090 such as in the example of FIG. 10. The example system 1350 includes a synthetic data aggregator 1355 which receives an output of synthetic data 1015, 1055 from a plurality of GANs 1-N 1012, 1052 provided from a plurality of participating sites 1002, 1042 to form the global dataset 1070. An A.I. model generator 1080 leverages the global dataset 1070 to train and test an output A.I. model 1090, such as a DNN 1090 trained and tested on the large, global dataset 1070 formed from synthetic data acquired from multiple sites. At each site, its available real data is used to generate the synthetic data 1015, 1055 aggregated to form the global dataset 1070. The dataset 1070 and/or the model 1090 can be output for use by one or more sites in one or more applications, for example.

Using the systems 1300 and 1350, a large dataset of synthetic data can be generated, tested with respect to a plurality of A.I. models, and aggregated to form a large dataset, mimicking a multi-site real dataset but not including real data so that patient privacy and other legal (e.g., HIPAA, etc.) concerns/compliance are protected. While DNN models are not capable of generating synthetic data from real data, incorporating one or more GANs into a DNN-based system provides new technology to the deep learning network system to enable the system to generate synthetic data that resembles real data and can train and test a learning network in the same way as real data while not exposing real data across multiple sites to invasion of privacy, fraud, and other legal concerns. Thus, A.I. models can be robustly and reliably generated on a large dataset of synthetic data generated from a small sample of real data.

In certain examples, synthetic data from a single site provides volume but not variation. By combining synthetic data from multiple sites, both volume and variation can be achieved in the global dataset 1070 to robustly train, test, and deploy one or more A.I. models 1090. If the individual site's data set does not include enough variation (e.g., to cover an entire statistical distribution of values, etc.), only known unknowns are explored by the model. However, by combining synthetic data from multiple sites, variation emerges, and unknown unknowns can be covered by the resulting models. In certain examples, the single model 1090 can be deployed to all sites 1002, 1042 so that all sites leverage the same A.I. model 1090 formed from the aggregation of their respective synthetic data 1015, 1055. If a training/testing data set is not robust, the model can collapse and end up being trained on repetitions of the same image. Aggregating synthetic generated data across sites helps to ensure a robust, varied dataset for thorough training of a resulting A.I. model, for example.

Figure 14:
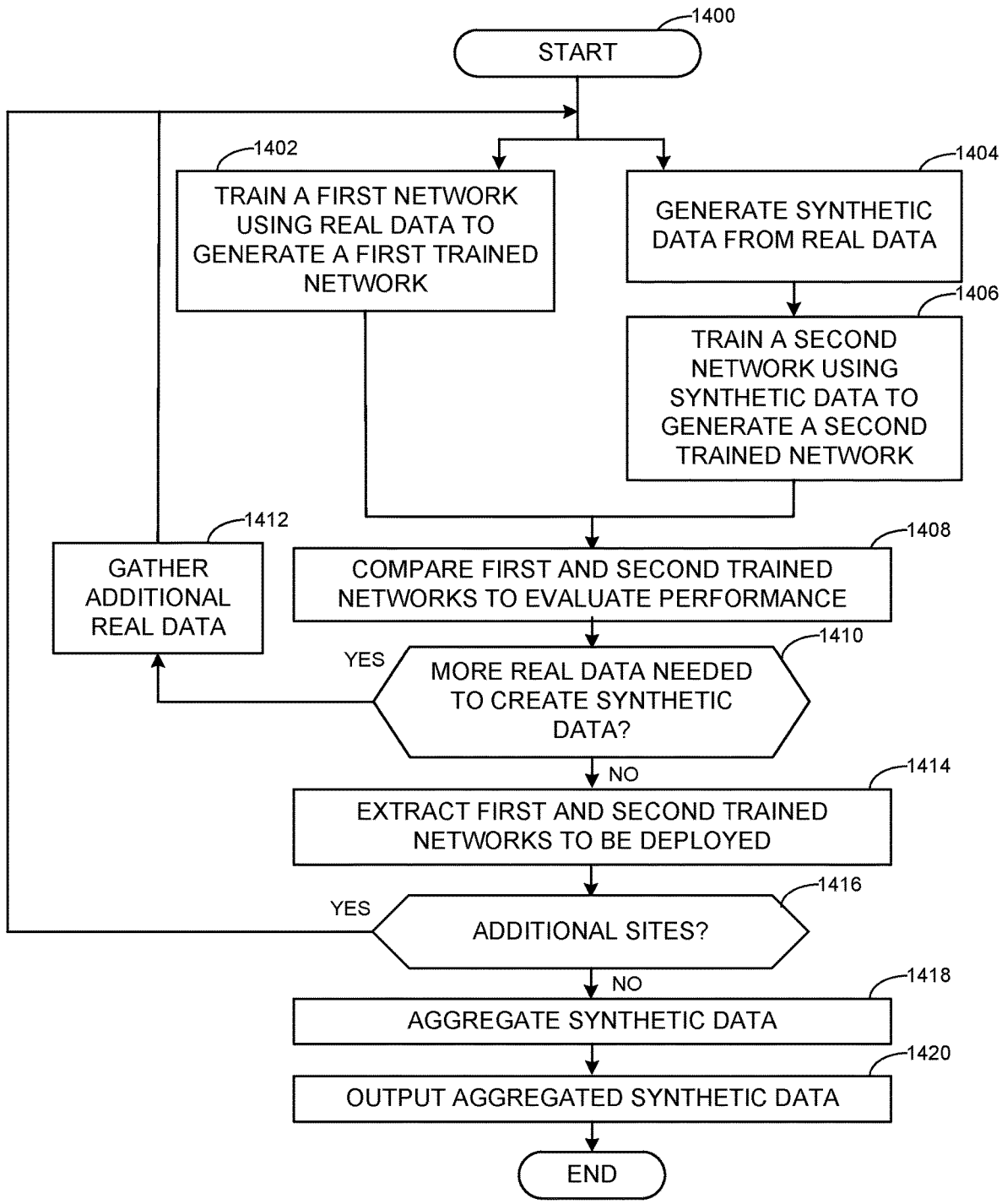
FIG. 14 illustrates a flow diagram for synthetic data generation at a healthcare provider's site using interaction between real data training and synthetic data training to produce secure, legal, compliant artificial intelligence models.

FIG. 14 illustrates a flow diagram of an example method 1400 for synthetic data generation at a healthcare provider's site using interaction between real data training and synthetic data training to produce secure, legal, HIPAA-compliant A.I. models. At block 1402, at a first site, a first network is trained on real medical data 1004, 1044 (e.g., image data, non-image medical data, patient demographic data, usage data, etc.) with respect to a clinical purpose to obtain a first trained network. For example, the first network is trained at the first site (e.g., a first hospital, etc.) with respect to image data processing such as shown in the example of FIGS. 2-6 above.

At block 1404, synthetic data is generated from real data. For example, a GAN 1012, 1052, 1100, 1315 can produce a synthetic data 1014, 1054 output by processing a real data 1004, 1044 input. The GAN takes the real data and uses the real data to form synthetic data based on a seed such as a latent code, random variable, etc., to form synthetic data that cannot be distinguished from real data when processed. By producing synthetic data that is indistinguishable in form, content, usability, etc., from actual medical data (e.g., image data, patient data, workflow data, monitoring data, etc.), the synthetic data produced by the GAN can be used to train A.I. models just as real data can. Thus, a large, robust data set can be formed from a small amount of protected real data.

At block 1406, a second network is trained on synthetic data to obtain a second trained network. For example, the synthetic data is used in place of real data to train and test a DNN and/or other A.I. network to generate an A.I. model. While the available amount of real data would be insufficient to reliably train an A.I. network, the larger amount of synthetic data can train and test an A.I. network for reliable deployment of the A.I. model for use in a clinical situation.

At block 1408, the first trained network and second trained network are compared to evaluate their performance. For example, the evaluator 1020, 1060, 1325 compares the first and second trained DNNs 1010, 1018, 1050, 1058 to determine whether the first network trained on real data is indistinguishable and/or otherwise comparable to the second network trained on synthetic data (e.g., accuracy, precision, consistency, etc.).

At block 1410, based on the evaluation, whether more real data is needed to create additional synthetic data is determined. For example, if the synthetically-trained second network does not match the accuracy and/or other performance of the real-trained first network, then more synthetic data is needed to train the second network. More real data can be leveraged to generate that additional synthetic data via the GAN, for example.

At block 1412, if more data is to be generated, then, additional real data is gathered to generate additional synthetic data by training a network model with the additional real data. For example, real data from a second site can be gathered and used to generate additional synthetic data, which can be pooled in a global dataset 1070 for training of the DNN 1090.

At block 1414, the first trained network and the second trained network are extracted as network models to be deployed. For example, the two trained networks are deployed as one module from the site.

At block 1416, control returns to block 1402 to repeat the process for additional available sites. Deployed trained network models can be deployed from each available site 1002, 1042 and centralized for coordinated operation.

At block 1418, aggregated synthetic data can be generated from the deployed trained network models, which are collected from different sites. For example, the global dataset 1070 is formed by aggregating synthetic data 1014, 1054 from each site 1002, 1042.

At block 1420, the aggregated synthetic data can be output to assist in neural network training. For example, the aggregated synthetic data of the dataset 1070 can be used to train a deep neural network 1090 for deployment as an A.I. model in a clinical setting (e.g., such as the deep learning device models of FIGS. 7A-7C, etc.).

While example implementations are illustrated in conjunction with FIGS. 1-14, elements, processes and/or devices illustrated in conjunction with FIGS. 1-14 may be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components disclosed and described herein are shown in conjunction with at least FIG. 14. In the examples, the machine readable instructions include a program for execution by a processor such as a processor 1512 shown in the example processor platform 1500 discussed below in connection with FIG. 15. The program may be embodied in machine readable instructions stored on a tangible computer readable storage medium such as a CD-ROM, a floppy disk, a hard drive, a digital versatile disk (DVD), a Blu-ray disk, or a memory associated with the processor 1512, but the entire program and/or parts thereof could alternatively be executed by a device other than the processor 1512 and/or embodied in firmware or dedicated hardware. Further, although the example program is described with reference to the flowchart illustrated in conjunction with at least FIG. 14, many other methods of implementing the components disclosed and described herein may alternatively be used. For example, the order of execution of the blocks may be changed, and/or some of the blocks described may be changed, eliminated, or combined. Although the flowchart of at least FIG. 14 depicts example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) of at least FIG. 14 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) of at least FIG. 14 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 15A:
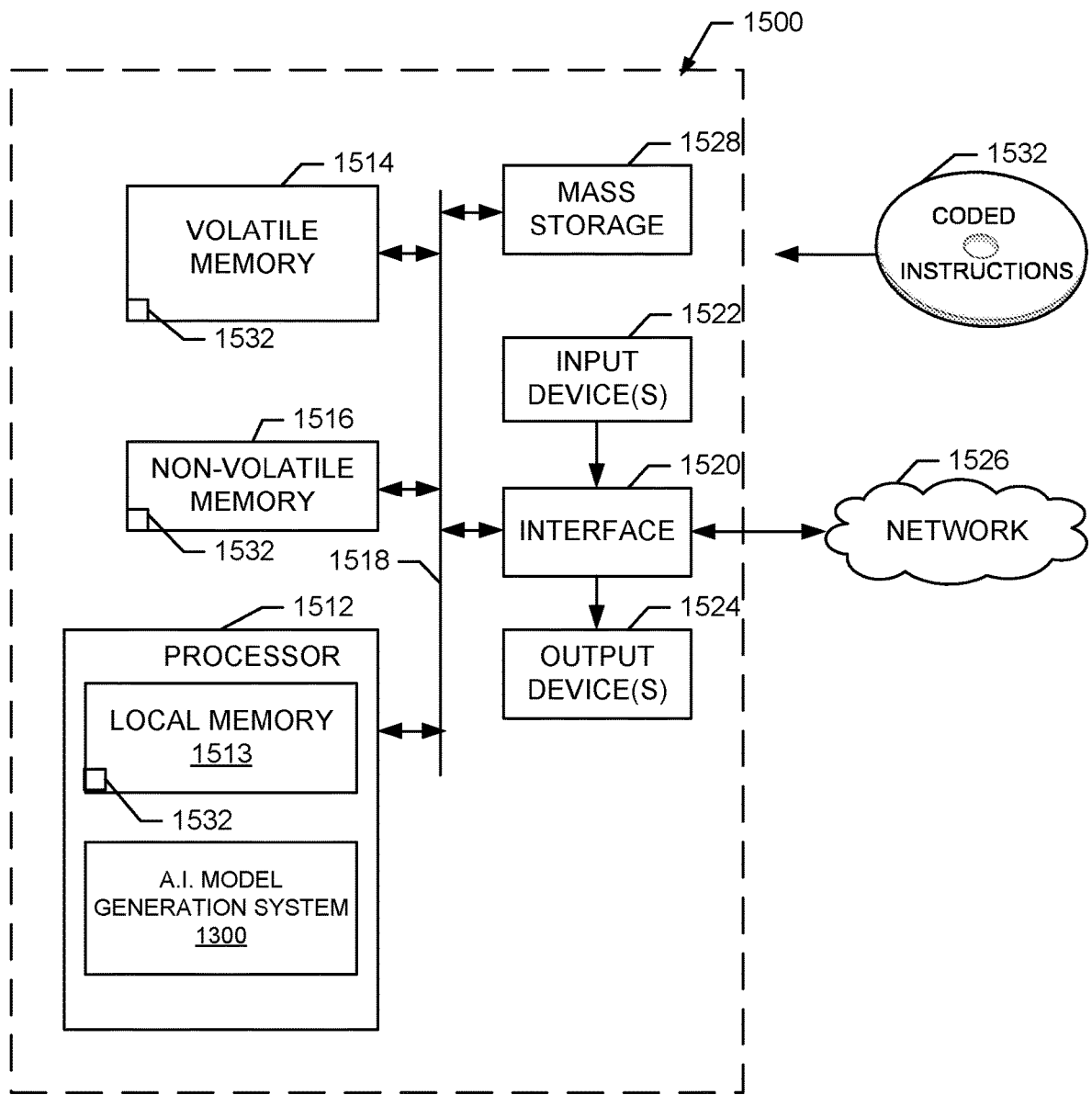
FIGS. 15A-15C are block diagrams of a processor platform structured to execute the example machine readable instructions to implement components disclosed and described herein.
Figure 15B:
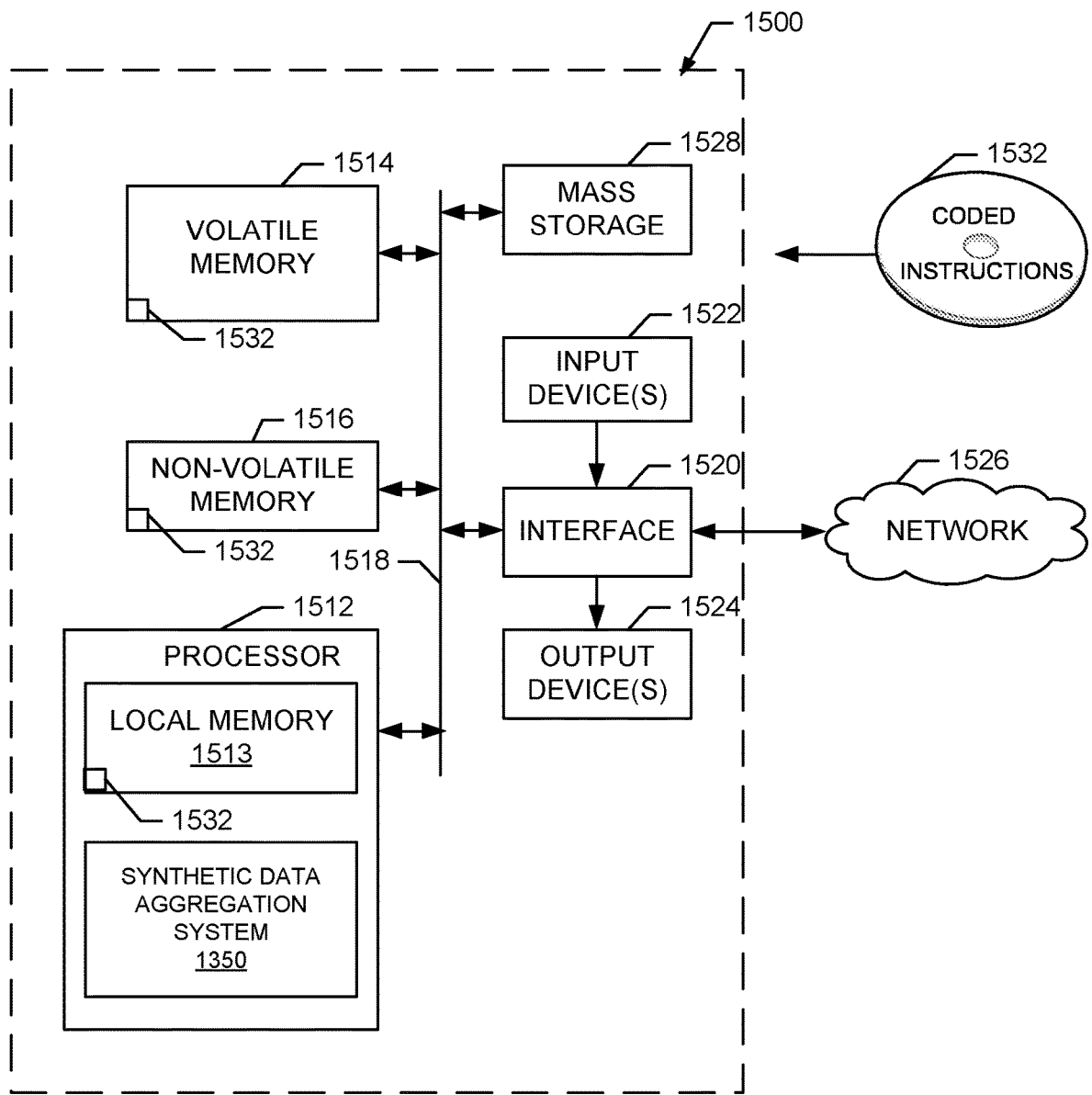
Figure 15C:
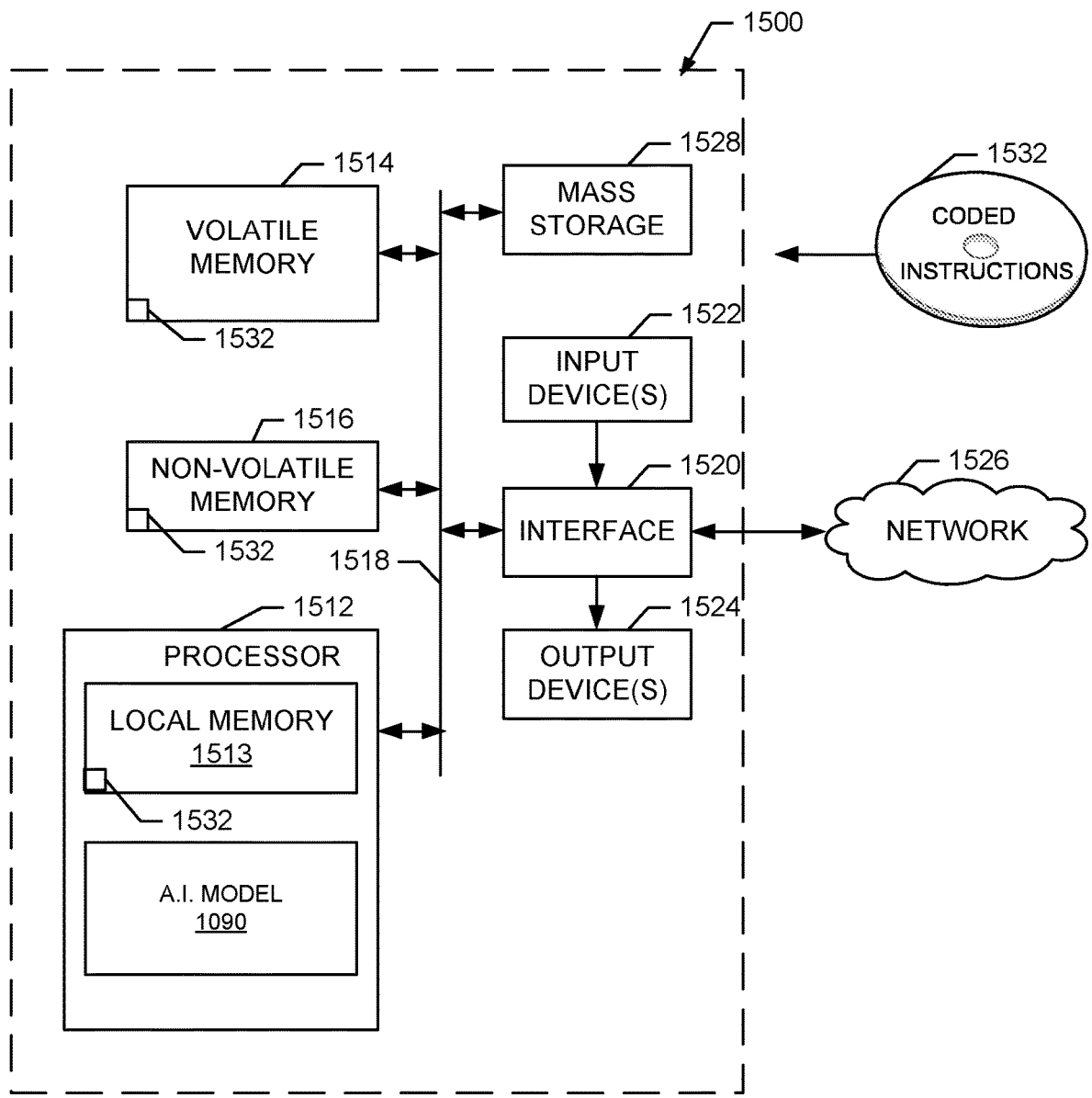

FIGS. 15A-15C are block diagrams of an example processor platform 1500 structured to executing the instructions of at least FIG. 14 to implement the example components disclosed and described herein. The processor platform 1500 can be, for example, a server, a personal computer, a mobile device (e.g., a cell phone, a smart phone, a tablet such as an iPad™), a personal digital assistant (PDA), an Internet appliance, or any other type of computing device.

The processor platform 1500 of the illustrated example includes a processor 1512. The processor 1512 of the illustrated example is hardware. For example, the processor 1512 can be implemented by integrated circuits, logic circuits, microprocessors or controllers from any desired family or manufacturer.

The processor 1512 of the illustrated example includes a local memory 1513 (e.g., a cache). The example processor 1512 of FIGS. 15A-15C executes the instructions of at least FIG. 14 to implement the example A.I. model generation system 1300 (FIG. 15A), data aggregation system 1350 (FIG. 15B), A.I. model 1090 (FIG. 15C), etc. In certain examples, a plurality of processors 1512 and/or processor platforms 1500 can be used to implement individual components of the example A.I. model generation system 1300 at one or more sites. The processor 1512 of the illustrated example is in communication with a main memory including a volatile memory 1514 and a non-volatile memory 1516 via a bus 1518. The volatile memory 1514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1516 may be implemented by flash memory and/or any other desired type of memory device. Access to the main memory 1514, 1516 is controlled by a clock controller.

The processor platform 1500 of the illustrated example also includes an interface circuit 1520. The interface circuit 1520 may be implemented by any type of interface standard, such as an Ethernet interface, a universal serial bus (USB), and/or a PCI express interface.

In the illustrated example, one or more input devices 1522 are connected to the interface circuit 1520. The input device(s) 1522 permit(s) a user to enter data and commands into the processor 1512. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 1524 are also connected to the interface circuit 1520 of the illustrated example. The output devices 1524 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1520 of the illustrated example, thus, typically includes a graphics driver card, a graphics driver chip or a graphics driver processor.

The interface circuit 1520 of the illustrated example also includes a communication device such as a transmitter, a receiver, a transceiver, a modem and/or network interface card to facilitate exchange of data with external machines (e.g., computing devices of any kind) via a network 1526 (e.g., an Ethernet connection, a digital subscriber line (DSL), a telephone line, coaxial cable, a cellular telephone system, etc.).

The processor platform 1500 of the illustrated example also includes one or more mass storage devices 1528 for storing software and/or data. Examples of such mass storage devices 1528 include floppy disk drives, hard drive disks, compact disk drives, Blu-ray disk drives, RAID systems, and digital versatile disk (DVD) drives.

The coded instructions 1532 representing the instructions executable for the method of FIG. 14 may be stored in the mass storage device 1528, in the volatile memory 1514, in the non-volatile memory 1516, and/or on a removable tangible computer readable storage medium such as a CD or DVD, for example.

From the foregoing, it will be appreciated that the above disclosed methods, apparatus, and articles of manufacture have been disclosed to generate, train, test, and deploy artificial intelligence models using a small amount of real data to produce a large data set of synthetic data. The disclosed methods, apparatus and articles of manufacture improve the efficiency of using a computing device by providing a model-based mechanism to process a small amount of real data to produce a large amount of synthetic data that resembles and functions as real data yet does not include the real data, thus satisfying legal, regulatory, privacy, and compliance requirements. The disclosed methods, apparatus and articles of manufacture are accordingly directed to one or more improvement(s) in the functioning of a computer. Further, a new type of data is generated to improve the computer's ability to train, test, and deploy robust neural networks and/or other A.I. models.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An artificial intelligence model generation system comprising:
    a deep neural network (DNN) generator to generate a first DNN model using first real data;
    a synthetic data generator to generate first synthetic data from the first real data, the first synthetic data to be used by the DNN generator to generate a second DNN model;
    an evaluator to evaluate performance of the first DNN model and the second DNN model based on output of the first DNN model and the second DNN model, the evaluator to determine whether to generate second synthetic data based on a comparison of a first output of the first DNN model and a second output of the second DNN model, the synthetic data generator to generate third synthetic data from a first site when the comparison indicates that performance of the first DNN model and performance of the second DNN model are aligned;
    a synthetic data aggregator to aggregate the third synthetic data from the first site and fourth synthetic data from a second site to form a synthetic data set; and
    an artificial intelligence model generator to generate and deploy an artificial intelligence model trained and tested using the synthetic data set.

2. The system of claim 1, further including a generative adversarial network (GAN) generator to generate a GAN model to be used by the synthetic data generator to generate the third synthetic data.

3. The system of claim 1, wherein, when the evaluator determines to generate second synthetic data, the synthetic data generator is to generate the second synthetic data using second real data obtained from a real data store.

4. The system of claim 1, wherein the synthetic data aggregator is to aggregate the third synthetic data and the fourth synthetic data across a plurality of sites to form the synthetic data set to be deployed to each of the plurality of sites.

5. The system of claim 4, wherein the artificial intelligence model generator is to generate and deploy the artificial intelligence model to each of the plurality of sites.

6. The system of claim 1, wherein the DNN generator is to generate the first DNN model according to a clinical purpose.

7. The system of claim 1, wherein the evaluator is to compare the first output of the first DNN model and the second output of the second DNN model by evaluating an accuracy of the second output compared to the first output.

8. The system of claim 1, wherein the first synthetic data resembles the first real data in content and format but does not include any portion of the first real data.

9. A non-transitory computer-readable storage medium comprising instructions which, when executed, cause at least one processor to implement at least:
    a deep neural network (DNN) generator to generate a first DNN model using first real data;
    a synthetic data generator to generate first synthetic data from the first real data, the first synthetic data to be used by the DNN generator to generate a second DNN model;
    an evaluator to evaluate performance of the first DNN model and the second DNN model based on output of the first DNN model and the second DNN model, the evaluator to determine whether to generate second synthetic data based on a comparison of a first output of the first DNN model and a second output of the second DNN model, the synthetic data generator to generate third synthetic data from a first site when the comparison indicates that performance of the first DNN model and performance of the second DNN model are aligned;
    a synthetic data aggregator to aggregate the third synthetic data from the first site and fourth synthetic data from a second site to form a synthetic data set; and
    an artificial intelligence model generator to generate and deploy an artificial intelligence model trained and tested using the synthetic data set.

10. The non-transitory computer-readable storage medium of claim 9, wherein the instructions, when executed, further cause the at least one processor to implement a generative adversarial network (GAN) generator to generate a GAN model to be used by the synthetic data generator to generate the first synthetic data.

11. The non-transitory computer-readable storage medium of claim 9, wherein, when the evaluator determines to generate second synthetic data, the synthetic data generator is to generate the second synthetic data using second real data obtained from a real data store.

12. The non-transitory computer-readable storage medium of claim 9, wherein the synthetic data aggregator is to aggregate the third synthetic data and the fourth synthetic data across a plurality of sites to form the synthetic data set to be deployed to each of the plurality of sites.

13. The non-transitory computer-readable storage medium of claim 12, wherein the artificial intelligence model generator is to generate and deploy the artificial intelligence model to each of the plurality of sites.

14. The non-transitory computer-readable storage medium of claim 9, wherein the DNN generator is to generate the first DNN model according to a clinical purpose.

15. The non-transitory computer-readable storage medium of claim 9, wherein the evaluator is to compare the first output of the first DNN model and the second output of the second DNN model by evaluating an accuracy of the second output compared to the first output.

16. The non-transitory computer-readable storage medium of claim 9, wherein the first synthetic data resembles the first real data in content and format but does not include any portion of the first real data.

17. A method comprising:
    generating, using at least one processor, a first DNN model using first real data;
    generating, using the at least one processor, a first synthetic data from the first real data;
    generating, using the at least one processor, a second DNN model using the first synthetic data;

evaluating, using the at least one processor, performance of the first DNN model and the second DNN model based on output of the first DNN model and the second DNN model, the evaluating to determine whether to generate second synthetic data based on a comparison of a first output of the first DNN model and a second output of the second DNN model;

generating, using the at least one processor when the comparison indicates that performance of the first DNN model and performance of the second DNN model align, third synthetic data from a first site;

aggregating, using the at least one processor, the third synthetic data from the first site and fourth synthetic data from a second site to form a synthetic data set; and deploying, using the at least one processor, an artificial intelligence model trained and tested using the synthetic data set.

18. The method of claim 17, further including generating a generative adversarial network (GAN) model to be used to generate the first synthetic data.

19. The method of claim 17, further including generating the second synthetic data using second real data obtained from a real data store.

20. The method of claim 17, wherein aggregating the first synthetic data and the second synthetic data includes aggregating synthetic data across a plurality of sites to form the synthetic data set and deploying the synthetic data set to each of the plurality of sites.

* * * * *